United States Patent
Gastfriend et al.

(10) Patent No.: US 11,521,736 B1
(45) Date of Patent: Dec. 6, 2022

(54) SYSTEM AND METHOD FOR ENCOURAGING THERAPEUTIC PSYCHOSOCIAL ACTIVITY

(71) Applicant: DynamiCare Health, Inc., Boston, MA (US)

(72) Inventors: Eric Gastfriend, Cambridge, MA (US); David Gastfriend, Newton, MA (US); Lawrence Reisler, Bet Shemesh (IL); Amardeep Ranu, Caledon (CA)

( * ) Notice: Subject to any disclaimer, the term of this patent is extended or adjusted under 35 U.S.C. 154(b) by 35 days.

(21) Appl. No.: 17/122,119

(22) Filed: Dec. 15, 2020

Related U.S. Application Data

(63) Continuation-in-part of application No. 15/620,423, filed on Jun. 12, 2017, now abandoned.

(60) Provisional application No. 62/349,214, filed on Jun. 13, 2016.

(51) Int. Cl.
| | |
|---|---|
| G16H 20/70 | (2018.01) |
| G16H 10/20 | (2018.01) |
| G16H 50/30 | (2018.01) |

(52) U.S. Cl.
CPC ............ *G16H 20/70* (2018.01); *G16H 10/20* (2018.01); *G16H 50/30* (2018.01)

(58) Field of Classification Search
CPC . G06F 19/3418; G06F 19/3475; A61B 5/083; A61B 5/7275; G16H 20/70; G16H 50/30; G16H 10/20
See application file for complete search history.

(56) References Cited

U.S. PATENT DOCUMENTS

| | | |
|---|---|---|
| 4,843,377 A | 6/1989 | Fuller et al. |
| 5,295,491 A | 3/1994 | Gevins |
| 5,349,187 A | 9/1994 | Azzazy |
| 5,980,447 A | 11/1999 | Trudeau |
| 6,039,688 A | 3/2000 | Douglas et al. |
| 6,072,396 A | 6/2000 | Gaukel |
| 6,559,769 B2 | 5/2003 | Anthony et al. |
| 6,748,792 B1 | 6/2004 | Freund et al. |
| 6,947,794 B1 * | 9/2005 | Levine ............... A61N 1/3712 607/28 |
| 7,962,342 B1 | 6/2011 | Coughlan et al. |
| 8,249,311 B2 | 8/2012 | Endo et al. |
| 8,280,436 B2 | 10/2012 | Harris |
| 9,228,997 B2 | 1/2016 | Keays |
| 9,250,228 B2 | 2/2016 | Nothacker et al. |
| 9,272,713 B1 | 3/2016 | Dvoskin |
| 9,302,179 B1 | 4/2016 | Merzenich |
| 9,317,662 B2 | 4/2016 | Bangera et al. |

(Continued)

*Primary Examiner* — Malina D. Blaise
(74) *Attorney, Agent, or Firm* — Mark F. Smith; Smith Brandenburg Ltd

(57) ABSTRACT

A system for encouraging therapeutic psychosocial activity of a patient comprising a master control system having a processor for operating system software, one or more portable communication devices in communication with the master control system, a testing device having testing input software that operates to transmit information to the master control system, wherein the master control system operates to transmit an information request to the one or more portable communication devices to direct the testing input software to create a window on a display screen informing the patient information has been requested, and the testing device operates to collect and transmit test information in response to the information request.

19 Claims, 35 Drawing Sheets

(56) References Cited

U.S. PATENT DOCUMENTS

| | | |
|---|---|---|
| 9,675,275 B2 | 6/2017 | Utley |
| 9,848,061 B1 * | 12/2017 | Jain .................. H04L 67/34 |
| 10,034,608 B1 * | 7/2018 | Dintenfass ............ G16H 30/40 |
| 10,937,528 B2 * | 3/2021 | Mian ...................... G16H 50/70 |
| 11,056,242 B1 * | 7/2021 | Jain ...................... G16H 10/60 |
| 11,384,398 B2 * | 7/2022 | Grimm ................ C12Q 1/6886 |
| 2003/0004403 A1 | 1/2003 | Drinan et al. |
| 2008/0183502 A1 | 7/2008 | Dicks et al. |
| 2008/0201174 A1 | 8/2008 | Ramasubramanian |
| 2008/0314115 A1 | 12/2008 | Faulder et al. |
| 2009/0047697 A1 * | 2/2009 | Hess ...................... G01N 33/74<br>435/17 |
| 2010/0028210 A1 | 2/2010 | Ozaki |
| 2010/0204600 A1 | 8/2010 | Crucilla |
| 2010/0328066 A1 | 12/2010 | Walker |
| 2011/0047508 A1 | 2/2011 | Metzler |
| 2011/0257994 A1 * | 10/2011 | Givens .................. G16H 40/67<br>705/2 |
| 2011/0263947 A1 | 10/2011 | Utley |
| 2011/0304465 A1 | 12/2011 | Boult |
| 2012/0075094 A1 | 3/2012 | Keays |
| 2012/0157871 A1 | 6/2012 | Walden |
| 2013/0172691 A1 | 7/2013 | Tran |
| 2013/0216989 A1 | 8/2013 | Cuthbert |
| 2014/0278135 A1 * | 9/2014 | Pruss .................... G16B 20/20<br>702/19 |
| 2014/0279721 A1 | 9/2014 | Siegel |
| 2014/0322164 A1 * | 10/2014 | Bloomgren ...... G01N 33/56983<br>424/85.4 |
| 2015/0084774 A1 | 3/2015 | Wojcik |
| 2015/0157276 A1 * | 6/2015 | Gratacos ................ A61B 5/486<br>600/301 |
| 2015/0212063 A1 * | 7/2015 | Wojcik .................. G06V 40/167<br>340/576 |
| 2015/0245789 A1 * | 9/2015 | Dromerick ............ A61B 5/225<br>600/558 |
| 2015/0296336 A1 * | 10/2015 | Hiller ...................... G16H 40/63<br>340/539.13 |
| 2016/0081587 A1 | 3/2016 | Ghazarian |
| 2016/0115548 A1 * | 4/2016 | Goel ...................... A61B 10/04<br>514/249 |
| 2016/0125600 A1 | 5/2016 | Lee |
| 2016/0132652 A1 * | 5/2016 | Chapman Bates .... G16H 50/20<br>706/11 |
| 2016/0270656 A1 | 9/2016 | Samec |
| 2017/0067115 A1 * | 3/2017 | Goel ...................... G16H 10/60 |
| 2017/0173262 A1 | 6/2017 | Veltz |
| 2017/0265807 A1 * | 9/2017 | Stopek ............. A61B 5/150877 |
| 2017/0287353 A1 | 10/2017 | Kazemi |
| 2018/0064374 A1 * | 3/2018 | Givens .................. G16H 40/63 |
| 2018/0075219 A1 | 3/2018 | Klein |
| 2018/0090231 A1 * | 3/2018 | Liederman ............ G16H 80/00 |
| 2018/0310890 A1 * | 11/2018 | Li ........................ A61B 5/4842 |
| 2019/0141914 A1 * | 5/2019 | Nelson ................ A01K 11/008<br>703/11 |
| 2019/0295725 A1 * | 9/2019 | Morrow, Jr. .......... G01S 5/0027 |
| 2019/0355481 A1 * | 11/2019 | Lamb .................... G06N 7/005 |
| 2020/0013493 A1 * | 1/2020 | Moloney-Egnatios ......................<br>G16H 50/20 |
| 2020/0129107 A1 * | 4/2020 | Sharma .................. A61B 5/224 |
| 2020/0140953 A1 * | 5/2020 | Goel ........................ C12Q 1/68 |

\* cited by examiner

Step 1

Authorizing the user

The QR code will be used to authorize the use of the test. The authorized mobile application will send the test identifier (obtained from the QR code) to our remote server to confirm the test is assigned to the user.

FIG 31b

Step 2

Extracting the strips

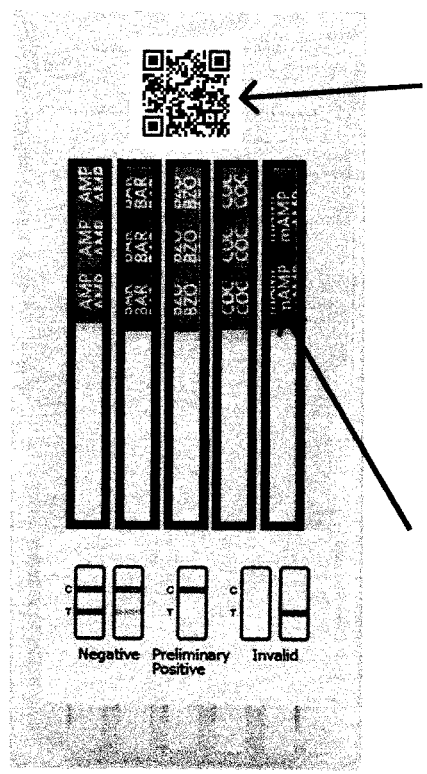

The QR code will be used to determine the test type and strip locations based on the test's specifications. This information will be retrieved from the remote server URL located on the QR code. Scale and rotation can be determined using image recognition software.

Each strip will be cropped and analyzed using steps 3 - 5.

The strip sticker can be used to determine the location of the strips without the QR code or device geometery. This allows automatic test reviewing of tests without QR codes if needed. However, obtaining exact coordinates from the remote server would be less error prone.

Step 3

Analyzing a strip

The end of the colored strip marks the beginning of the test strip area. The width of the strip is determined by the edges of the sticker. This can be determined using image processing software.

The test area's size is either provided by the test specifications or can be assumed to be some multiple of the strip width.

Step 4

Test and control line intensity

The pixel intensity is determined along the bisection line. Two peaks should appear. The first peak being the control line. The second peak being the test line.

An average pixel intensity is taken across the width of the strip for each location along the bisection line.

Step 5

Final results

The results are defined as the following:

- Positive: The test line intensity is at least half the control line's intensity.

- Negative: The test line intensity is less than half the control line's intensity.

- Invalid: There is no control line or the intensity of the test line is greater than the control line.

SYSTEM AND METHOD FOR ENCOURAGING THERAPEUTIC PSYCHOSOCIAL ACTIVITY

This application is a continuation-in part of U.S. patent application Ser. No. 15/620,423, filed Jun. 12, 2017 and claims benefit to and incorporates in its entirety U.S. Provisional Patent Application No. 62/349,214 filed Jun. 13, 2016.

BACKGROUND OF THE INVENTION

The subject invention is directed to a system and method for encouraging therapeutic psychosocial activity. In the field of addiction medicine, Contingency Management (CM) is a highly effective, evidence-based methodology for improving outcomes using the power of incentives. CM involves setting frequent (>1/week), objective goals (usually abstinence or participation in treatment), which patients can achieve to earn tangible rewards (such as cash or vouchers). There have been numerous studies that demonstrate its effectiveness. However, despite its effectiveness, CM is used consistently by less than 10% of treatment programs due to difficulties, such as the necessity for frequent drug testing, training for staff, and the difficulty of managing rewards on individual basis.

Traditionally, CM has been implemented using pre-determined schedules of when patients need to show up for treatment or take drug tests; manual tracking of patient abstinence (via in-person supervised drug tests) or treatment attendance (as recorded by treatment providers); and manual (pen-and-paper) calculation of the rewards due to each patient according to personalized reward schedules. Reward schedules and manual distribution of rewards/prizes are usually set up so that patients earn increasingly larger rewards as they stay sober/in treatment, but reset to a low base value if they miss treatment or fail a drug test. Further, random testing of patients is often difficult to administer and current systems do not operate effectively to provide a patient with instant rewards or provide healthcare workers the ability to monitor, track and test a patient in real time.

Automated versions of CM have been developed and have reduced the amount of required staff support. Such systems operate to calculate rewards for patients that have passed drug testing. Systems have also been developed which utilize webcams on personal computers to enable patients to record a video of their drug tests (such as by use of a carbon monoxide detector) from home, which obviates the need for manual, in-person drug tests. However, such systems require a pre-set schedule for drug tests (typically twice per day with an 8-hour interval in between). Other systems utilize portable communication devices, such as a smartphone or tablet, making testing procedures more portable and convenient. However, such systems do not operate to predict when randomized testing should be requested such as when a patient is at a high risk for acute relapse or hospitalization within an impending time frame. Further, prior art systems do not operate effectively to use patient information to generate a profile for performing a prediction analysis to arrive at an outcome, to monitor the patient in real-time and to send requests (such as information and testing requests) to the patient that maximizes the likelihood of achieving the desired outcome. Accordingly, the benefits of random testing are minimized. In addition, rewards for patients passing such tests are typically awarded by mail. Accordingly, patients must wait before receiving the reward. It has been found that separating the time of testing from receipt of a reward reduces the effectiveness of the reward system.

Accordingly, it would be desirable to have a system and method for encouraging therapeutic psychosocial activity that minimizes the amount of staff or in-person support; that maximizes the benefits of random testing; that provides real-time testing and rewards to create instant gratification and a greater therapeutic effect.

SUMMARY OF THE INVENTION

The subject invention is a system for encouraging therapeutic psychosocial activity of a patient, the system comprising: a master control system having a processor for operating system software; a portable communication device for use by a patient, the communication device is in communication with the master control system through a communication network; a testing device having testing software that operates to communicate with the master control system for transmitting test information to the master control system; wherein the master control system operates to transmit a notice for requested information to the portable communication device informing the patient that information has been requested; and wherein the notice for requested information includes compliant requirements, such as a time period during which the patient must respond to the notice for requested information.

In a preferred embodiment of the invention the testing device operates to collect testing information and transmit the test information in response to the notice for requested information to the master control system.

In another preferred embodiment of the invention the testing device is a device that operates to measure breath alcohol of the patient, such as a breathalyzer.

In a preferred embodiment of the invention the testing device is a carbon monoxide (CO) monitor.

In another preferred embodiment of the invention the testing device operates to test for drug use by the patient, such as but not limited to a saliva testing device.

In another preferred embodiment of the invention the testing device is a digital quiz designed to test the understanding of the patient with regard to a therapeutic activity.

In another preferred embodiment of the invention the testing device is a digital survey that the patient can periodically complete, designed to collect clinically relevant information about the patient, to be presented to their healthcare provider and used for predictive analysis.

In another preferred embodiment of the invention the testing device is a video device for obtaining a video of the patient taking prescribed medications, to ensure proper medication adherence.

In another preferred embodiment of the invention, the testing device is an imaging device for taking a photograph of the patient's prescription drug supplies to ensure that the patient has the appropriate supplies of medication and is not diverting medication to inappropriate uses.

In a preferred embodiment of the invention the system for encouraging therapeutic psychosocial activity of a patient further comprises a tracking device that operates to verify that the patient is at a pre-set location at a pre-set time for participating in a desired therapeutic psychosocial activity.

In another preferred embodiment of the invention the tracking apparatus operates for real-time tracking of the location of the portable communication devices.

In another preferred embodiment of the invention the desired therapeutic psychosocial activity is selected from the list consisting of performing a test, attending a therapy session, a self-help group meeting, and a medical appointment.

In a preferred embodiment of the invention the system for encouraging therapeutic psychosocial activity of a patient further comprises an identification system for identifying and verifying the identity of the patient using the portable communication device and/or the testing device.

In a preferred embodiment of the invention the identification system is in the form of an imaging device for obtaining the facial image of the patient utilizing the portable communication device and transmitting the image to the master control system.

In another preferred embodiment of the invention the identification system is in the form of a video device for obtaining a video of the patient showing the facial image of the patient and/or the patient performing a function.

In another preferred embodiment of the invention the function performed by the identification device is to show that the patient using the testing device.

In another preferred embodiment of the invention the identification device is in the form of a fingerprint reader that operates to generate an image of the fingerprint of the patient and transmits the image to the master control system.

In another preferred embodiment of the invention the identification device is in the form of a voice recognition device.

In another preferred embodiment of the invention the identification device is in the form of a biomedical device, such as, but not limited to, DNA recognition, iris recognition, or other biomedical devices.

In another preferred embodiment of the invention the master control system includes analytics software that operates to receive information, generate a profile and perform a real-time prediction analysis to create a prediction outcome for the patient.

In a preferred embodiment of the invention the analytics software operates in cooperation with calendar information to create the prediction outcome.

In another preferred embodiment of the invention the prediction analysis creates a predetermined schedule for testing of a patient and a schedule for transmitting one or more requests to the portable communication device of the patient in accordance with the predetermined schedule for testing or whenever the prediction analysis of the patient determines that a predictive uncertainty or a predicted risk reaches a predetermined threshold.

In a preferred embodiment of the invention the prediction analysis operates to determine a schedule for testing, a schedule for transmitting one or more requests for a test, and to request tests whenever predictive uncertainty or predicted risk reaches a predetermined threshold, so that the testing schedule is optimized to monitor and encourage psychosocial behavior goals with fewer tests and that such tests are performed when they are most needed to minimize the likelihood of acute relapse or hospitalization.

In another preferred embodiment of the invention the analytics software operates in cooperation with a tracking system to modify in real-time the prediction analysis and prediction outcome based on the location of the patient.

In another preferred embodiment of the invention the system software of the master control system operates in cooperation with the prediction analysis software to send out notices to third parties concerning a patient.

In a preferred embodiment of the invention the system for encouraging therapeutic psychosocial activity of a patient further comprises one or more service providers.

In a preferred embodiment of the invention the one or more service providers include a financial provider that operates to receive financial information for depositing funds into a deposit account of a patient.

In a preferred embodiment of the invention the one or more service providers includes a financial provider that operates to transfer funds (reward) into a rewards account of a patient.

In another preferred embodiment of the invention the master control system is in communication with a patient's financial sources for receiving information concerning a withdrawal and/or deposit of funds into a patient's account.

In another preferred embodiment of the invention the master control system is in communication with a patient's financial sources for receiving information concerning a purchase by a patient.

A preferred embodiment of the invention the system for encouraging therapeutic psychosocial activity comprises a master control system having a processor for operating system software and a portable communication device in communication with the master control system through a communication network. Preferably, one or more service providers communicate with the master control system through the communication network. The portable communication device includes a testing device that operates to collect test information and transmits the testing information to the master control system. In operation, the master control system transmits notices for requested information to the portable communication device of a patient informing the patient that information has been requested. Preferably, the notices for requested information include compliant requirements such as a time period that the requested information must be transmitted to the master control system.

A preferred embodiment of the invention is a system for encouraging therapeutic psychosocial activity of a patient for changing a habit or a certain behavior of the patient, the system comprising: a master control system having a processor for operating system software; a portable communication device for use by the patient, the portable communication device is in communication with the master control system through a communication network; and a testing device that operates to communicate with the master control system; wherein the portable communication device includes an identification system that operates to obtain identification information simultaneously with the operation of the testing device; wherein the master control system operates to transmit a notice for requested test information to the portable communication device which operates to inform the patient of the requested test information; wherein the master control system operates to perform a prediction analysis to determine if the patient is at a high risk or a low risk of violating a condition of treatment and wherein the requested test information is transmitted to the portable communication device on a random and on a predetermined schedule and wherein the number of requests for the requested test information is increased when the prediction analysis determines that the patient is at a high risk of violating the condition of treatment or decreased when the prediction analysis determines the patient is at a low risk of violating the condition of treatment; wherein the testing device operates to obtain the requested test information; and wherein the obtained requested testing information and the identification information is transmitted to the master control system which operates to determine if the patient is in compliance with a condition for treatment.

In a preferred embodiment of the invention the notice for the requested test information includes a time period informing the patient when the requested test information is transmitted to the master control system.

In another preferred embodiment of the invention the system further comprises a transmittal schedule for scheduling notices for information and wherein the transmittal schedule is created using statistical model.

In a preferred embodiment of the invention the master control system operates to transmit to the portable communication device a request that the patient participate in an activity as a pre-set location and at a pre-set time and wherein the portable communication device includes a tracking system that operates to verify that the patient is at the pre-set location at the pre-set time to participate in the activity.

In a preferred embodiment of the invention the tracking system monitors and transmits the location of the patient and determines if the patient will arrive at a pre-set location at the pre-set time.

In a preferred embodiment of the invention, the tracking system operates to determine the amount of time the patient was at a pre-set location and transmits the amount of time to the master control system which operates to determine if the patient remained at the pre-et location for a required amount of time.

In a preferred embodiment the system for encouraging therapeutic psychosocial activity includes a pattern recognition system that operates with the testing device to make determinations with regard to a test being conducted by a patient.

A preferred embodiment of a system for encouraging therapeutic psychosocial activity of a patient for changing a habit or a certain behavior of the patient, the system comprises a master control system; a portable communication device for use by the patient, the portable communication device is in communication with the master control system through a communication network; and a testing device that operates to obtain test information; wherein the portable communication device operates to transmit test information and identification information to the master control system; wherein the master control system operates to transmit one or more notices for requested test information to the portable communication device which operates to inform the patient that test information has been requested; wherein the master control system includes analytics software that operates to use test information to create a predicted outcome that includes a predictive risk; wherein the one or more notices for requested test information are transmitted to the portable communication device on a random and on a predetermined schedule and wherein the analytics software operates to increase or decrease the number of the one or more notices for the requested test information to be transmitted to the portable communication device based on the predicted outcome; and wherein the analytics software further operates to compare test information obtained from a patient to previous test information obtained from the patient and then determines if there is any inconsistency.

In a preferred embodiment the one or more notices for the requested test information includes a time period informing the patient when the requested test information is to be transmitted to said master control system.

In a preferred embodiment the system for encouraging therapeutic psychosocial activity of the patient further comprises an identification system having an imaging device that operates with the portable communication system to stream real time video to the master control system and wherein the master control system has recognition software that operates to identify the patient and further operates to determine if the patient at any time taking a requested test was out of view of the imaging device, and wherein if the recognition software determines that the patient was out if view of the imaging device at any time while taking the requested test, the master control system then operates to send a notice to the patient that the requested test must be retaken.

In a preferred embodiment the system for encouraging therapeutic psychosocial activity further comprises an identification system having an imaging device that operates with the portable communication system to stream real time video to the master control system and wherein the master control system has recognition software that operates to identify the patient and further operates to determine if a requested test and the patient at any time while taking the requested test was out of view of the imaging device, and wherein if the recognition software determines that the requested test or the patient was out if view of the imaging device at any time while taking the requested test, the master control system then operates to send a notice to the patient that the requested test must be retaken.

In a preferred embodiment the system for encouraging therapeutic psychosocial activity of the patient further comprises a tracking system for obtaining tracking information of the patient and wherein the master control system operates to transmit one or more notices for the patient to attend a therapeutic psychosocial activity at a preset location and at a preset time and wherein the master control system operates to use the tracking information determine a current location of the patient and to determine if the patient will be at the preset location at the preset time, and if the master control system determines that the patient will not be at the preset location at the preset time, the master control system operates to find an alternative therapeutic psychosocial activity and examines a schedule for the patient and reschedules the therapeutic psychosocial activity based on the available alternative therapeutic psychosocial activity and the schedule for the patient.

In a preferred embodiment the imaging device takes images or a video of the patient and wherein the master control system operates to use the images or the video to make a predicted outcome that indicates the physical and/or emotional state of the patient.

In a preferred embodiment the master control system further transmits to the portable communication device a request that the patient participate in a therapeutic psychosocial activity at a pre-set location and at a pre-set time and wherein the portable communication device further comprises a tracking system that operates to verify that the patient is at the pre-set location at the pre-set time to participate in said therapeutic psychosocial activity and wherein the master control system cooperates with the tracking system to determine a time period that the patient was at the preset location and compares the time period with a scheduled time period for the therapeutic psychosocial activity to determine if the patent attended the therapeutic psychosocial activity for the entire scheduled time period.

A preferred embodiment the system for encouraging therapeutic psychosocial activity of a patient comprises: a master control system; a portable communication device for use by the patient, the portable communication device is in communication with the master control system; a testing device having testing software for obtaining test information and is coupled to the portable communication device which operates to communicate with the master control system and transmits the test information obtained by the testing device to the master control system; a tracking system in communication with the master control system and operates to track a location of the patient and to verify that the patient is at a preset location at a preset time and further operates determine an amount of time the patient is at the preset location and compare the amount of time the patient is at the preset location with a time duration of a therapeutic psychosocial activity to determine if the patient complied with a compliant requirement; and an identification system in communication with the master control system and operates to verify the identity of the patient using the testing device; wherein the master control system includes analytics software that operates to compare test information obtained from a patient to previous test information obtained for the patient and then determines if there is any inconsistency.

In a preferred embodiment the system for encouraging therapeutic psychosocial activity of the patient further comprises a service provider in communication with the master control system wherein the service provider operates to transfer a reward to a patient when the patient has completed a compliant requirement.

In a preferred embodiment the analytics software operates to create a prediction analysis and further operates in cooperation with the tracking system to modify the prediction analysis based on a patient location.

Various other objects, advantages, and embodiments of the invention will be apparent from the following description, the accompanying drawings, and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIGS. 31a-31e illustrate a saliva test strip such as used for performing a test of a patient, the patient uses the test strips which are in view and the patient are in view, preferably constant view of the imaging device and wherein images of the saliva test, as illustrated, are sent to the master control system which operates the analytics software and the recognition software for determining if the patient met a compliant requirement.

DESCRIPTION OF THE INVENTION

Figure 1:
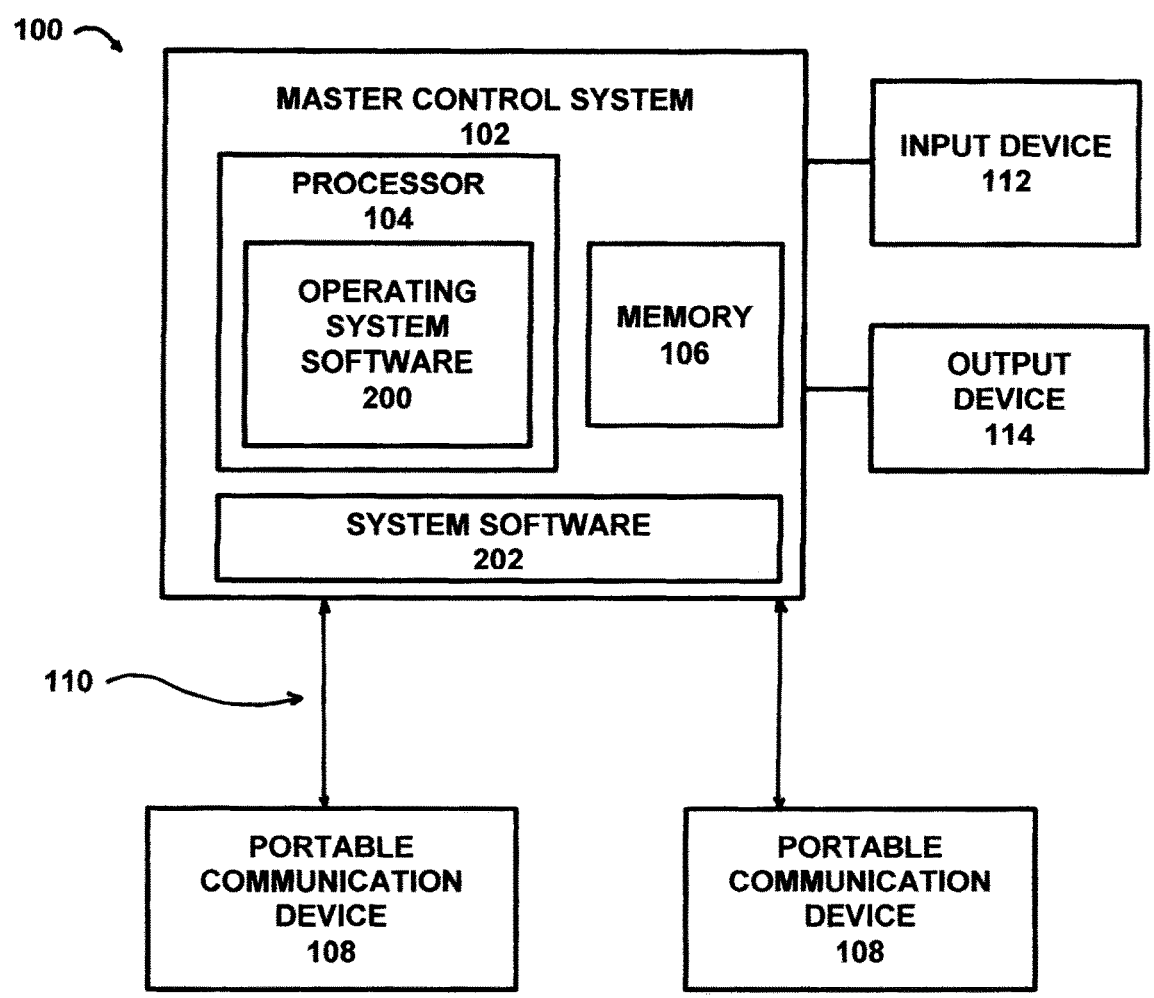
FIG. 1 is a general schematic representation of a preferred embodiment of a system for encouraging therapeutic psychosocial activity comprising a master control system having a processor for implementing operating system software, and a plurality of portable communication devices in communication with the master control system through a communication network.

The subject invention is a new and novel system and method for encouraging therapeutic psychosocial activity having a master control system with a processor for operating system software, and a plurality of portable communication devices in communication with the master control system through a communication network. The system further includes a testing device that operates to collect test information and transmit the test information to the master control system for use in creating a predictive outcome and possible intervention and/or for use by the master control system to provide an immediate reward to the patient. Preferably, the system for encouraging therapeutic psychosocial activity 100 uses a predetermined activity schedule 174 listing various therapeutic activities that are available. Using patient information 166, a patient profile 168 and calendar information 176 the master control system 102 creates a transmittal schedule 178 for the patient. The master control system 102 then operates to transmit to the patient's portable communication device 108 a notice 310 that test information 118 has been requested or that the patient is expected to attend a therapeutic psychosocial activity 130 as part of the patient's compliant requirements 136. Upon receiving a notice that test information 118 is requested, the patient can accept the request, using one or more menu options (fields) 190 displayed on the patient's portable communication device 108. If accepted, the patient uses an appropriate testing device 116 to obtain test information 118 which is transmitted to the master control system 102. In a preferred embodiment, the system for encouraging therapeutic psychosocial activity 100 includes an identification system 120 and operates to identify and/or verify the identity of the patient and has an imaging device 300 that operates to take a facial image 302 of the patient or operates to take a video 304 of the patient showing the facial image 302 of the patient over a period of time. Preferably, the imaging device 300 operates in cooperation with the patient's portable communication device 108 to stream real time video 304 to the master control system 102 that uses recognition software 306 of the identification software 206 to identify the patient, such as by recognizing the face of a patient, to ensure that the test is being performed by the correct patient. The recognition software 306 further operates to determine if at any time the patient P taking the test is or was out of view of the imaging device 300 during the taking of the test and/or before the test information 118 was transmitted to the master control system 102. If the master control system 102 using the recognition software 306 determines that the patient was out of view of the imaging device 300 at any time while the test was being performed or prior to test information 118 being transmitted to the master control system 102, the master control system 102 operates to send a notice 308 to an operator, such as an assigned therapist or health care worker, suggesting that the test information 118 could be fake and the test should be retaken by the patient. In another preferred embodiment of the invention the system for encouraging therapeutic psychosocial activity 100 further comprises a tracking system 124 which can be used determine the current location 125 of the patient. Preferably, real-time tracking information 134 is utilized by a healthcare worker to determine if a patient is moving in the direction a pre-set location 126 but will not be on time (will not arrive at the pre-set location 126 at the pre-set time 128) and will miss all or a portion of the psychosocial activity 130. In the event the patient is unable to at arrive at the pre-set location at the pre-set time, the master control system 102 operates to determine when an alternative therapeutic psychosocial activity 130 and examines the patient's schedule 135 and reschedules the therapeutic psychosocial activity 130 for a new pre-set time 128 (and/or pre-set location 126). The amount of time that the patient is at a pre-set location 137 to participate in the therapeutic psychosocial activity 130 is then compared with the time duration of the activity 139 by the master control system 102 which then operates the analytics software 210 to determine if the patient has complied with predetermined compliant requirements 136. In a preferred embodiment of the invention the master control system 102 and each portable communication device 108 are in communication with one or more service providers 142 that transfer rewards funds from a deposit account 148 into a rewards account 152 of a patient as an award 164 for the patient when the patient has complied with a compliant requirement 136, such as passing a test or participating in a therapeutic psychosocial activity. In another preferred embodiment the master control system 102 includes analytics software 210 that operates to compare test information 118 obtained from a patient to previous test information obtained for the patient and then determines if there is any inconsistency. In another preferred embodiment, the master control system uses the recognition software 306 of the identification software 206 in cooperation with analytics software 210 to examine the facial image or video or the patient to make a predicted outcome 172, such as using the recognition software 306 for analyzing facial and body patterns and movements of the patient to calculate a predictive risk 182 and/or make a predicted outcome 172.

As used herein the terms "patient" or "patients" refer to anyone using the system for encouraging therapeutic psychosocial activity including, but not limited to a patient or patients receiving medical treatment, an individual or individuals that are under the control of a judicial court or a criminal system, an individual or individuals wishing to change a habit or a certain behavior, and an individual or individuals receiving treatment for undesirable life styles, such as tobacco, drug and/or alcohol abuse. In describing the preferred embodiments of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. It should be understood that unless specifically stated, the term "patient" and "individual" will refer to both a patient and an individual.

Referring to FIG. 1, the system for encouraging therapeutic psychosocial activity 100 is illustrated comprising a master control system 102 having a processor 104 that utilizes operating system software 200 which cooperates with and implements the psychosocial system software 202 of the system for encouraging therapeutic psychosocial activity of the present invention, a memory 106, and a plurality of portable communication devices 108 having an input/output screen 186 (FIG. 9) for communicating with the master control system 102 through a communication network 110. The master control system is coupled to other devices, such as a suitable input device 112, like a keypad, touch screen, or other input devices that can accept information and one or more conventional output devices 114, such as a computer display, printer, projection device, and the like. It should be understood that the master control system 102 can include any combination of the above components, or any number of different components, peripherals, and other devices. Preferably, the master control system 102 operates under the control of an operating system, such as the WINDOWS operating system developed by Microsoft Corporation, the Android operating system developed by Google, or the iOS operating system developed by Apple Computer Corporation. It should be understood, however, that other operating systems could be utilized to implement the psychosocial system software 202 of the system for encouraging therapeutic psychosocial activity 100 of the present invention.

System Software:

The psychosocial system software 202 is a computer-readable medium having computer-readable instructions for performing a method of operating the system for encouraging therapeutic psychosocial activity 100. Preferably, the psychosocial system software 202 is an interactive, menu and event driven system that uses prompt, dialog, and entry windows to guide a patient to enter information. As used herein, the term "software" refers to any form of programmed machine-readable language or instructions (e.g., object code) that, when loaded or otherwise installed, provides operating instructions to a machine capable of reading those instructions, such as a computer. The psychosocial system software 202 of the present invention can be stored or reside on, as well as be loaded or installed from, one or more flash drives, hard disks or any other form of suitable non-volatile electronic storage media. The psychosocial system software 202 can also be installed by downloading or other form of remote transmission, such as by using Local or Wide Area Network (LAN or WAN)-based, Internet-based, web-based or other remote downloading or transmission methods.

Figure 2:
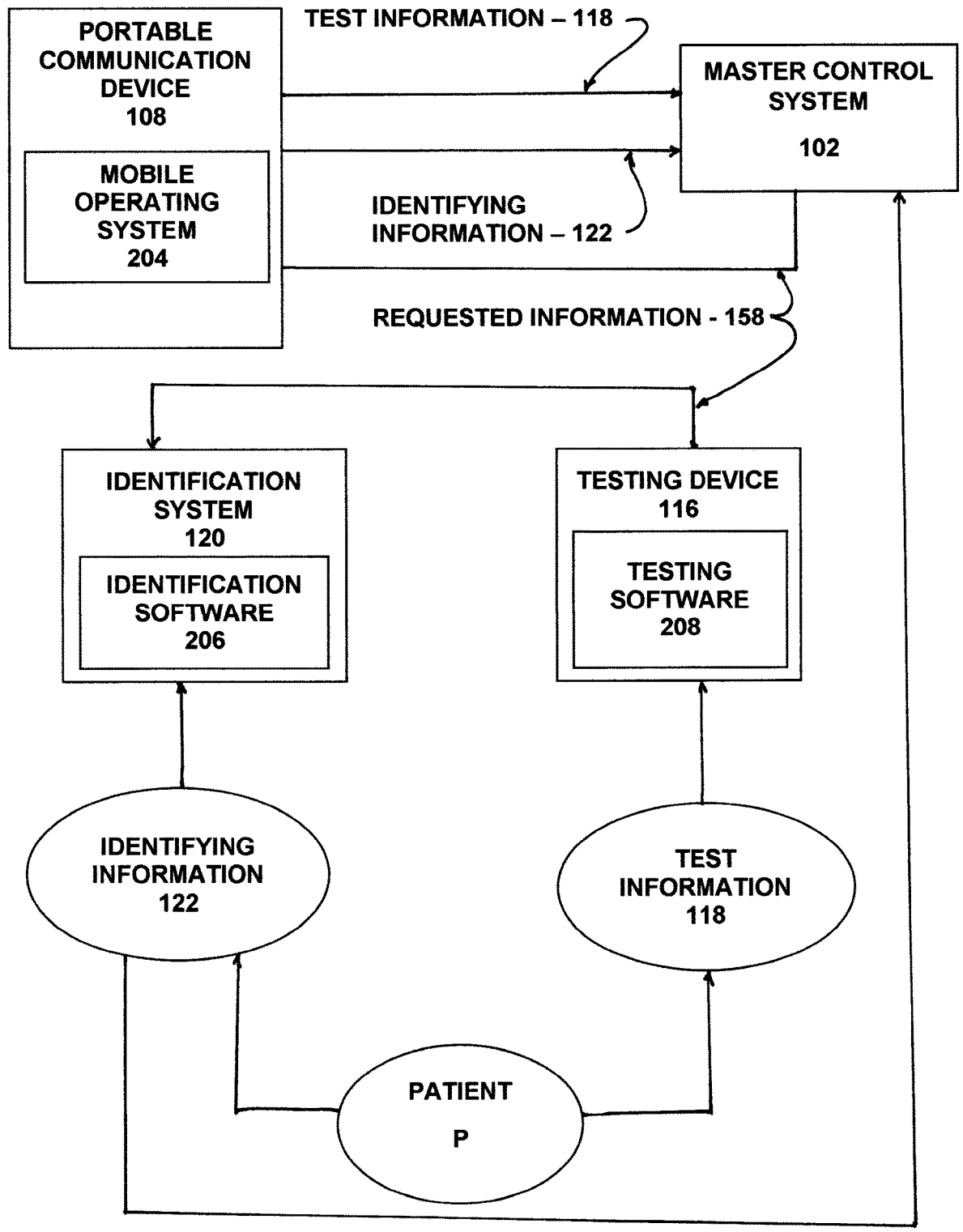
FIG. 2 is a schematic representation of a preferred embodiment of the system for encouraging therapeutic psychosocial activity of the subject invention showing a portable communication device for receiving a notice for requested information from the master control system and in communication with a testing device that operates to collect and transmit test information in response to the request and showing an identification system for obtaining identifying information for confirming the identity of the patient.

Portable Communication Devices:

Referring to FIG. 2, as illustrated each portable communication device 108 includes or is coupled to a testing device 116 that operates to obtain and transmit test information 118 to the master control system 102 through the communication network 110 which can be the communication network (such as a mobile phone carrier, such as VERIZON, AT&T, Internet connection, and the like) generally used by the portable communication device 108. The portable communication device as used herein includes various mobile communication systems, such as, but not limited to, smartphones, tablets, personal digital assistant (PDAs) and the like and are typically equipped with touchscreen, Bluetooth, Wi-Fi, GPS mobile navigation, camera, video camera, speech recognition, voice recorder capabilities. The portable communication device 108 operates using a mobile operating system 204, such as an operating system marked under the name ANDROID by Google or IOS by Apple, but it should be understood that other operating systems can be utilized. The testing device 116, utilizing appropriate testing software 208 for that particular device, cooperates with the mobile operating system 204 to operate the testing device 116 and transmit the collected test information 118 to the master control system 102. As shown, in a preferred embodiment each portable communication device 108 includes or is coupled with an identification system 120 having identification software 206 which operate to transmit identifying information 122 to the master control system 102 through the communication network 110 which can be the communication network (such as a mobile phone carrier, such as VERIZON, AT&T, Internet connection, and the like) generally used by the portable communication device 108.

Testing Device:

Preferably, the testing device 116 operates to obtain and transmit test information 118 directly to the master control system 102 such as by an internal system (i.e. system that uses a mobile phone carrier (not shown)) or through a portable communication device 108 using its mobile phone carrier to the master control system 102. The testing device 116 is included in or is coupled to the portable communication device 108 and in a preferred embodiment is in the form of a test component or device, such as used for measuring breath alcohol of the patient, such as a breathalyzer, or devices such as saliva test strips, chemical testing devices, health monitors, such as, but limited to, a device for measuring heart beats, blood pressure, voice recording devices, facial expression imaging devices, body movement devices, and other such devices. It should be understood that the testing device can also be in the form of an ethanol sensor, or a carbon monoxide (CO) monitor, or a digital quiz designed to test the understanding of patient to therapeutic activities, or a digital survey that a patient periodically completes and which is designed to collect clinically relevant information about the patient, or a video device effective for obtaining a video of a patient such as when the patient is taking a prescribed medication, or an imaging device for obtaining a photograph of a patient's prescription drug supply, or a combination of one or more components or devices. Accordingly, it should be understood that the testing device is not limited to such forms of components or devices but that other forms capable for testing various desired factors, such as alcohol, drugs, tobacco, activities, health or metabolic testing devices and components, may be utilized or a combination of testing devices effective for testing various desired factors may be utilized. It should also be understood that the testing device can also be in the form of computer-based materials (text, video and audio) having quizzes at the end of the computer-based material which function to verify that the patient completed the activity and fulfilled the compliant requirements for the activity.

Figure 29:
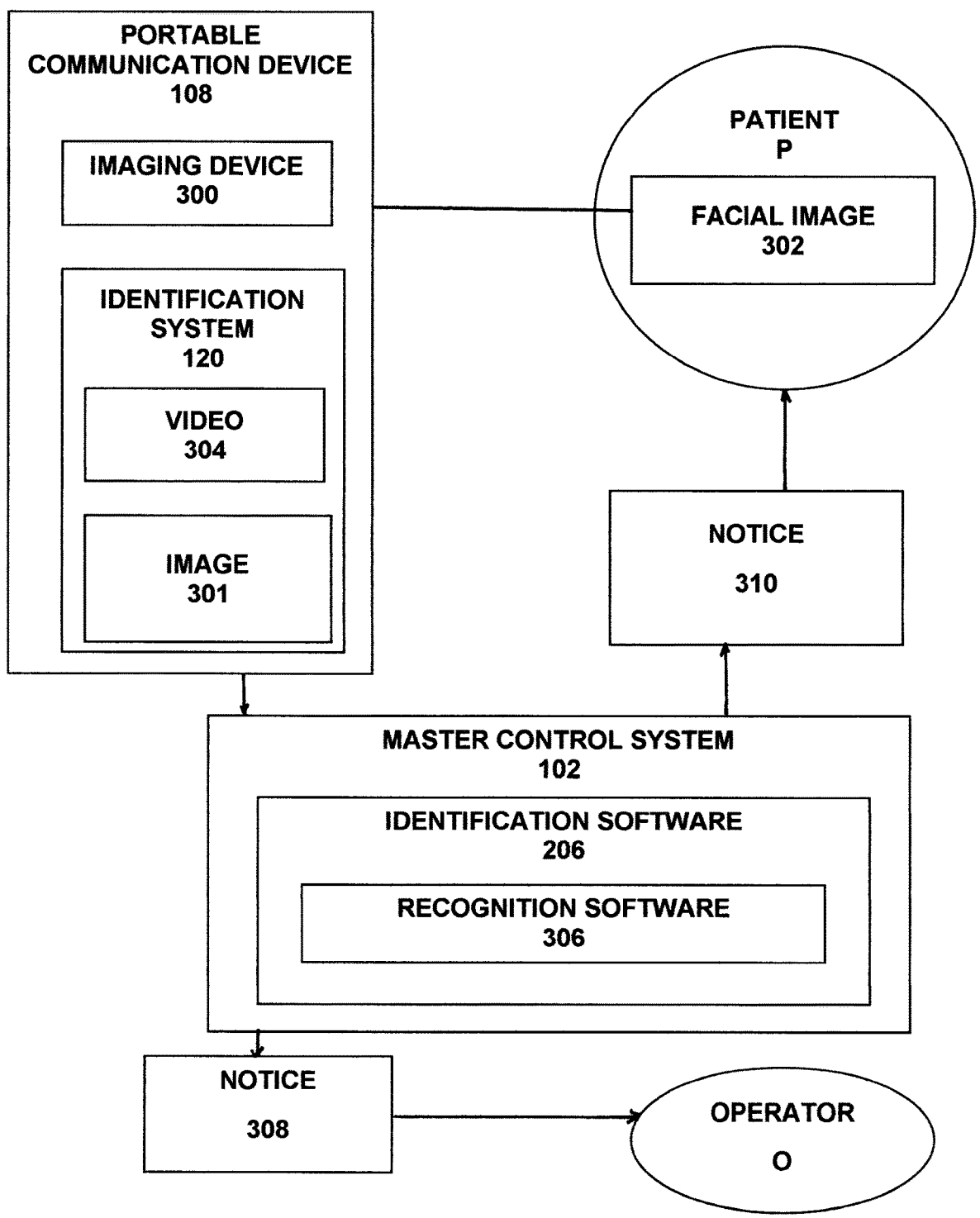
FIG. 29 is a schematic representation of the system for encouraging therapeutic psychosocial activity illustrating the master control system in communication with a patient communication device and having an identification system that includes a recognition software that operates with the identification system and testing device to make determinations with regard to a test being conducted by a patient.
Figure 30:
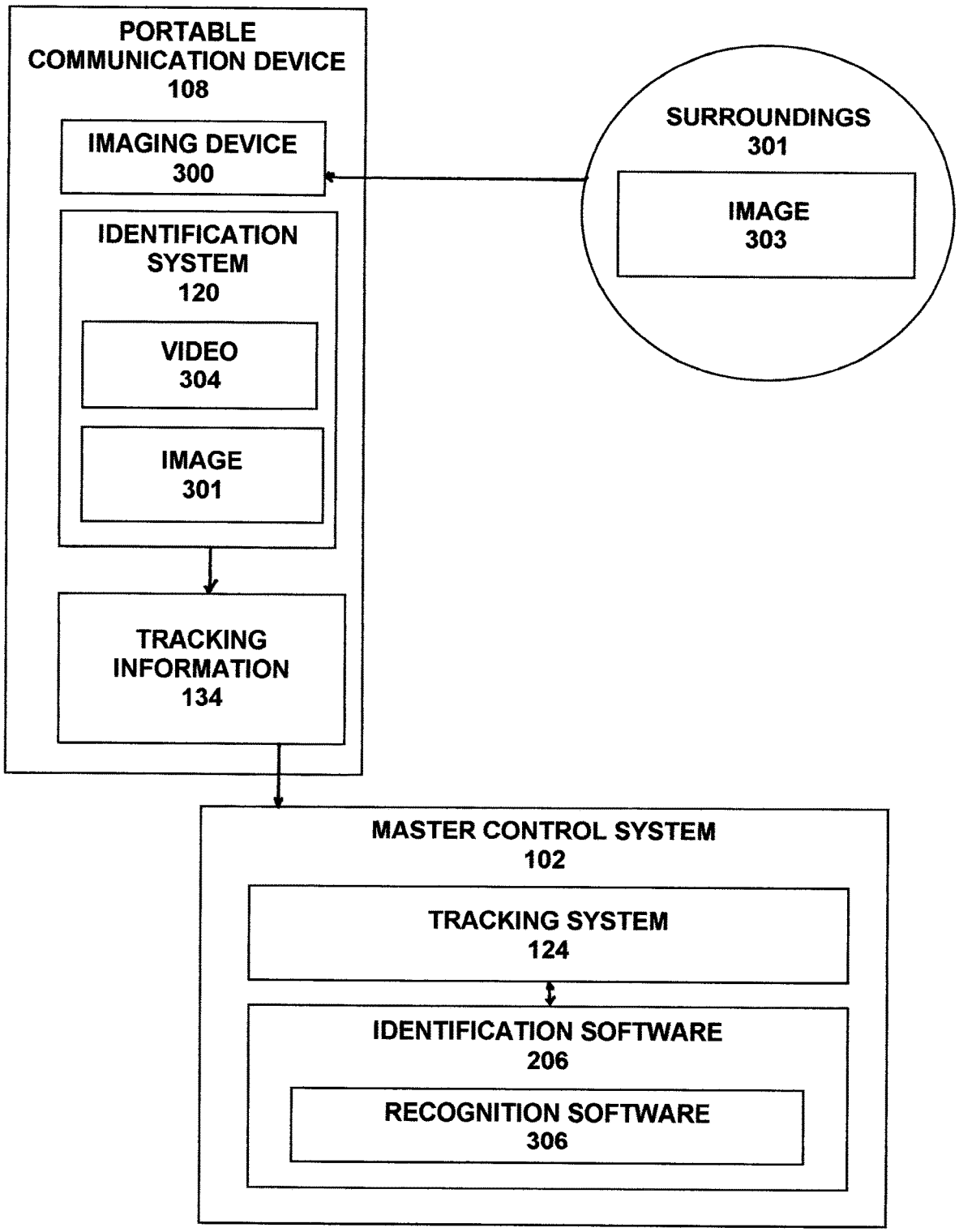
FIG. 30 is a schematic representation of the system for encouraging therapeutic psychosocial activity illustrating the interactions between a patient's portable communication device, an identification system, testing system, tracking system and the master control system.
Figure 31A:
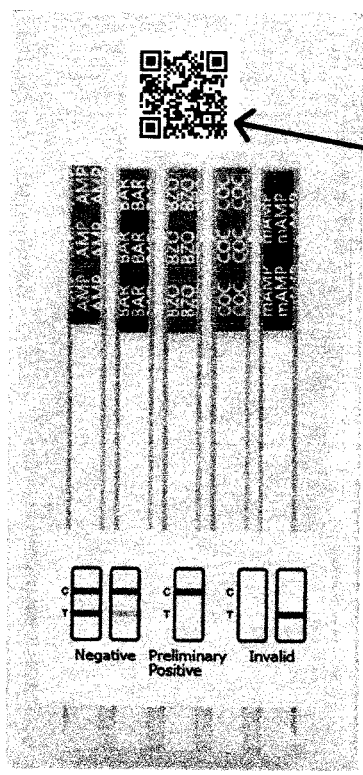
Figure 31C:
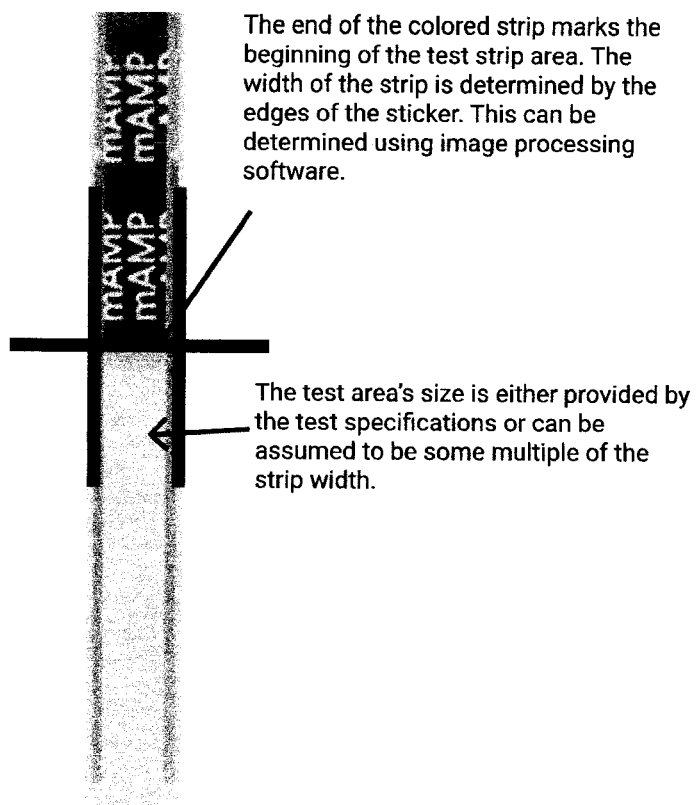
Figure 31D:
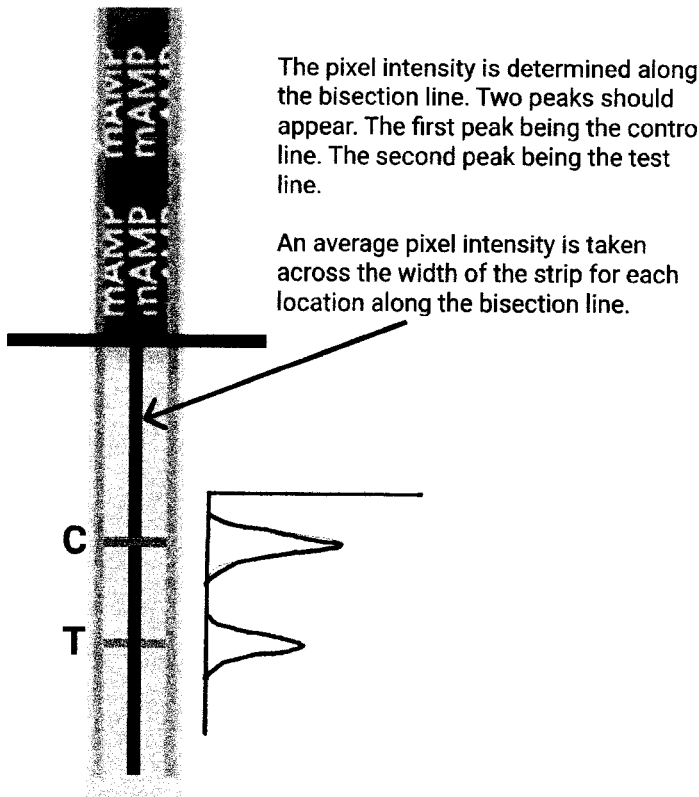
Figure 31E:
Figure 31E:
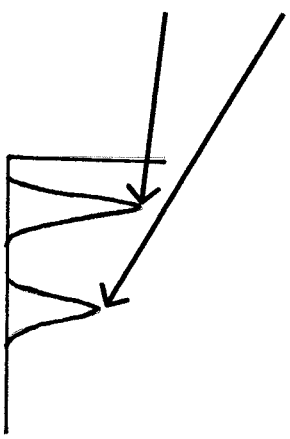

Identification System:

Referring to FIGS. 29 and 30, the identification system 120 preferably is incorporated in the portable communication device 108 or is coupled to the portable communication device 108 and operates to identify and/or verify the identity of the patient and preferably includes an imaging device 300 that in a preferred embodiment operates to take the facial image 302 of the patient or operates to take a video of the patient showing the facial image 302 of the patient over a period of time. In a preferred embodiment the identification system 120 can also include a fingerprint reader that operates to generate an image of the fingerprint of the patient, or a voice recognition device, or a biomedical device, such as, but not limited to, DNA recognition, iris recognition, or other biomedical devices, or a combination thereof. The identification system 120 operates to obtain identifying information 122 which is then transmitted by the identification system 120 directly to the master control system 102 such as by an internal system (i.e. system that uses a communication network 110 such as a mobile phone carrier (not shown)) or by the portable communication device 108 using its communication network 110 (such as a mobile phone carrier, such as VERIZON or AT&T) system (not shown). The psychosocial system software 202 of the master control system 102 then operates to examine the identifying information 122 and verifies the identity of the patient P, such as by comparing the identifying information with reference information (not shown). It should be understood that preferably the identifying information 122 is obtained simultaneously with the patient operating the testing device 116. For a non-limiting exemplary illustration, imaging device 300 of the identification system 120 is in the form of a video camera which functions to take a video 304 of the patient operating the testing device 116 and transmits the identifying information 122 (video) to the master control system 102 with test information 118 obtained by operation of the testing device 116.

Recognition Software

One problem often encountered with identification systems used for ensuring that a test has been or is being performed by a particular patient is that it is often possible for the patient taking the test or who took the test to substitute a test result (testing information) with another test result (substituted testing information) or have another individual take the test rather than the patient and transmit false testing information to the master control system. Accordingly, in a preferred embodiment of the invention, the imaging device 300 is in the form of a video camera that operates in cooperation with the patient's portable communication device 108 to stream real time video 304 to the master control system 102 that uses recognition software 306 of the identification software 206 to identify the patient, such as by recognizing the face of a patient, to ensure that the test is being performed by the correct patient P. The recognition software 306 further operates to determine if at any time the patient P taking the test is or was out of view of the imaging device 300 during the taking of the test and/or before the test information 118 was transmitted to the master control system 102, thus, allowing a patient to substitute another individual to take the test and transmit fake test information to the master control system. If the master control system 102 using the recognition software 306 determines that the patient P was out of view of the imaging device 300 (not continuously shown in the real time video 304) at any time (or for an amount of time that would allow a patient to have another individual perform a test) while the test was being performed or prior to test information 118 being transmitted to the master control system 102, the master control system 102 operates to send a notice 308 to an operator O, such as an assigned therapist or health care worker, suggesting that the test information 118 could be fake and the test should be retaken by the patient. In another preferred embodiment, the master control system 102 operates to send a notice 310 to the patient P using the patient's portable communication device 108 that another test needs to be performed. It should now be understood that by continuously observing the patient performing a test or observing the patient such that the patient is unable to allow another individual to take the test and transmit fake test information to the master control system ensures or reduces the likelihood that the test was not performed by the patient. Accordingly, the identification system 120 uses the imaging device 300 that operates in cooperation with the patient's portable communication device 108 to stream real time video 302 to the master control system 102 which uses recognition software 306 to identify, such as by recognizing the face of a patient, and provides a notice 308 to an operator if the patient P is out of view of the imaging device 300 anytime while taking the test. In another preferred embodiment the master control system 102 sends a notice 310 to the patient P that another test needs to be performed. It should now be apparent to one skilled in the art that by continuously (or such that another individual cannot be substituted for the patient) keeping the patient taking a test in view of the imaging device 300 ensures or reduces the likelihood that the patient assigned to take the requested test is taking the test and indeed another individual has not been substituted.

It should now be understood to one skilled in the art that preferably the imaging device 300 operates in cooperation with the patient's portable communication device 108 to stream real time video 304 of both the patient taking (performing) a test and the testing device 116 are being used for obtaining the test information 118 and cooperating with the patient's portable communication device 108 to transmit the test information 118 to the master control system 102. If the master control system 102 using the recognition software 306 of the identification software 206 determines that the patient or the testing being performed were out of view of the imaging device 300 at any time (or out of view for a period of time that would allow an individual to be substituted for taking a test or such that fake test information could be substituted for the test information), prior to the test information 118 being transmitted to the master control system 102, the master control system 102 sends a notice 308 to an operator O, such as an assigned therapist or health care worker, suggesting that the test information may be fake and a new test request should be sent to the patient. In another preferred embodiment, the master control system 102 sends a notice 310 to the patient which is displayed on the patient's portable communication device 108 that another test needs to be performed.

Preferably, the recognition software 306 is a pattern recognition software that operates and uses real time images or videos to detect and recognize a patient, track camera movements and produce a high resolution image (sufficient resolution to obtain image or video test information (where results of a test can be visibly shown, such as results using saliva test strips, as illustrated in FIGS. 31*a*-31*e*), and can track moving objects which can be used in determining if a patient or a test has been improperly substituted. One such pattern recognition software is OpenCV developed by Intel Corporation, Santa Clara, Calif.

In a non-limiting illustration of the operation of the system, a patient P, when receiving a notice for requested information 158 (FIG. 2), randomly or by a predetermined schedule, requiring a patient to perform an activity (such as using the test device), the portable communication device 108 and the testing device 116 operate to perform a test of the patient and collect test information 118. Prior to such testing, the identification software 206 functions to activate the identification system 120 which obtains identifying information 122, immediately before the patient is being tested, while being tested, and immediately after testing. The identifying information 122 is then transmitted to the master control system 102 which operates to use the recognition software 306 to identify the patient taking the test, monitor the patient while taking the test, monitor the test and the obtaining of test information 118. After receiving the test information, the master control system 102, operates using the psychosocial system software 202, to analyze the test information 118 to determine if the patient is in compliance with compliant requirements 136.

Figure 3:
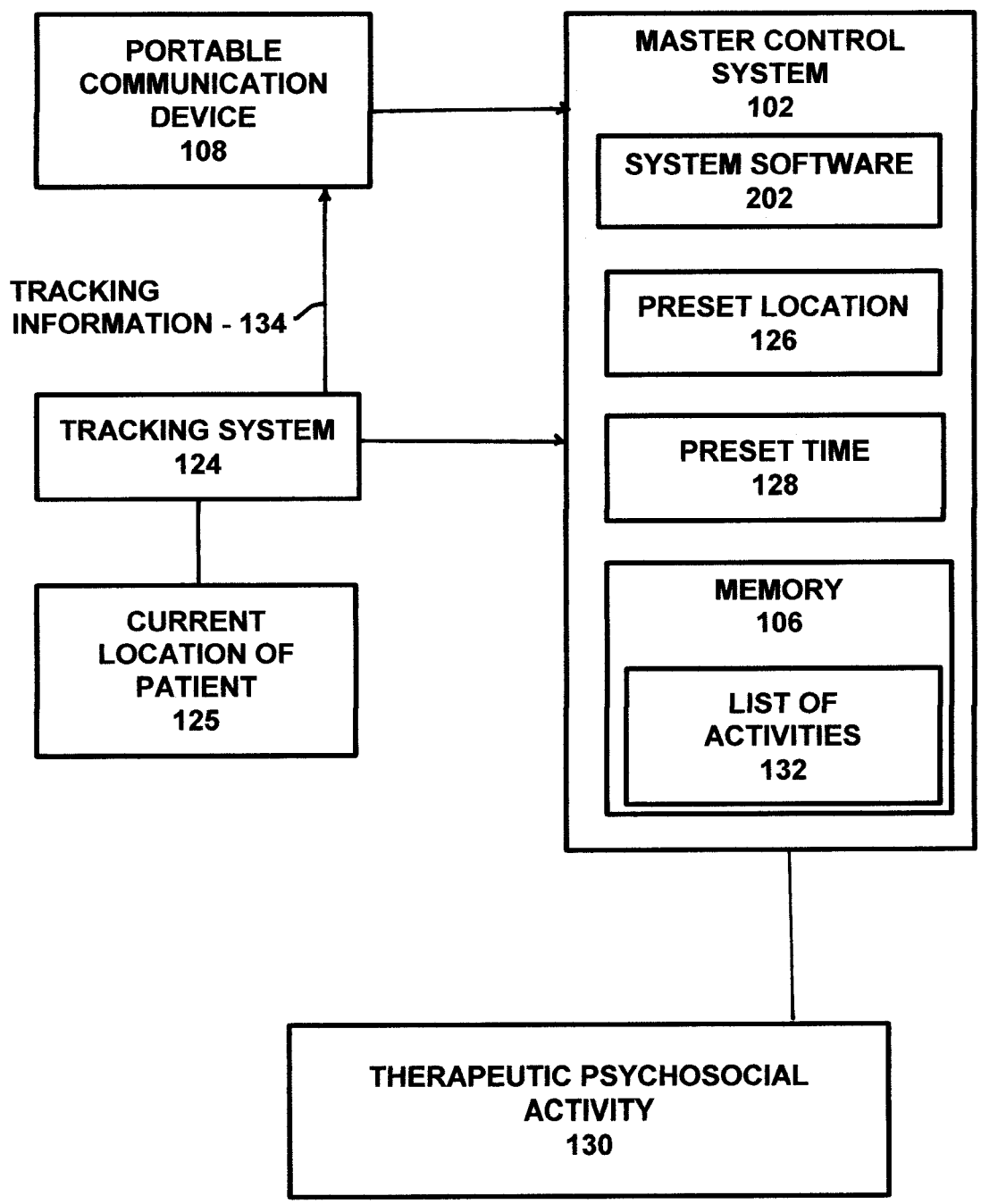
FIG. 3 is a schematic representation of a preferred embodiment of the system for encouraging therapeutic psychosocial activity wherein the master control system operates to transmit to a portable communication device a pre-set location and a pre-set time for a patient to perform an activity and having a tracking system that operates to track the current real-time location of the patient.
Figure 4:
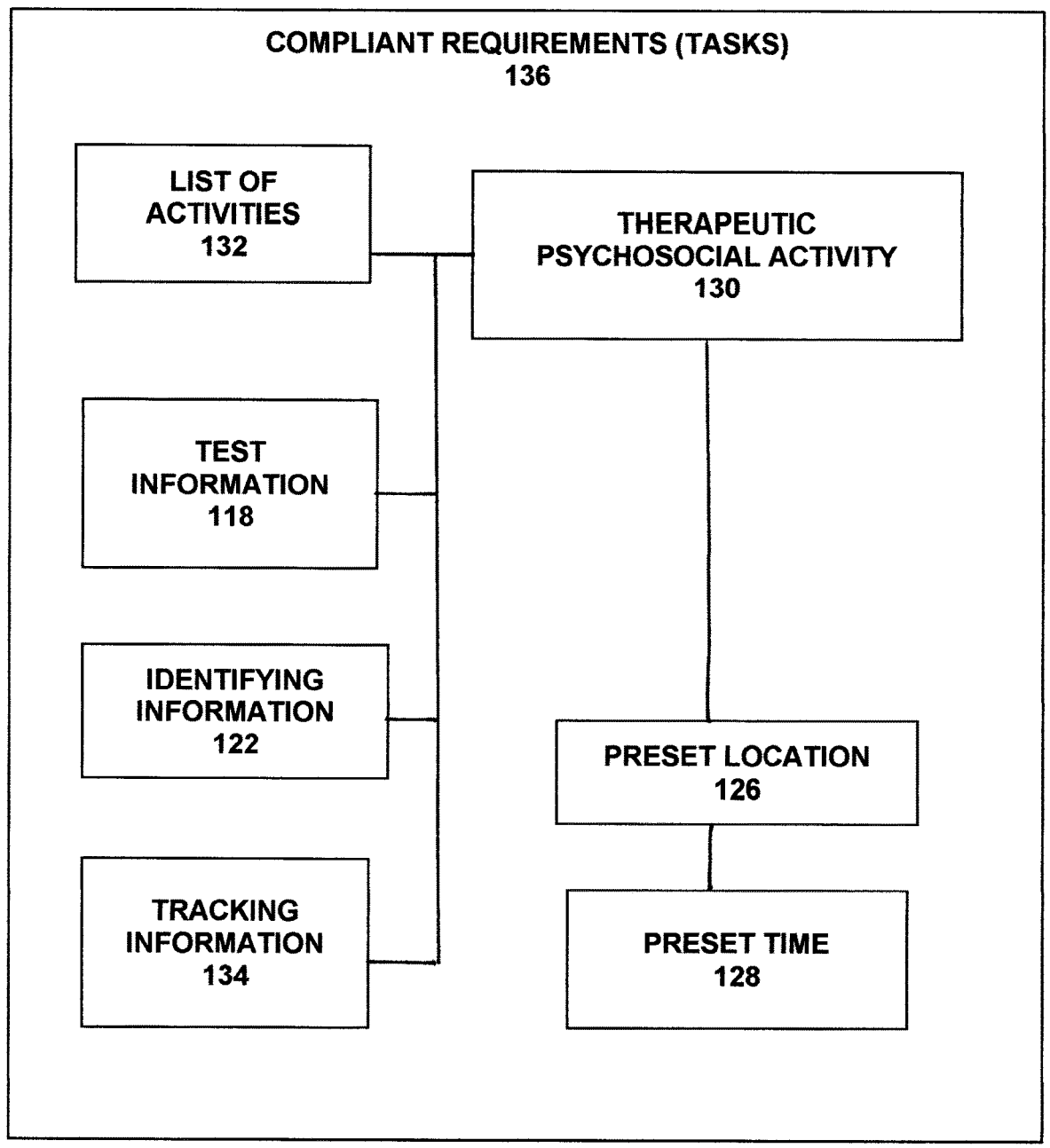
FIG. 4 is a schematic representation showing compliant requirements for a patient comprising various activities, test information, identifying information, tracking information that are used to determine if a patient should receive a reward.

Tracking System:

In another preferred embodiment of the invention, as illustrated in FIG. 3, the system for encouraging therapeutic psychosocial activity 100 further comprises a tracking system 124, for a non-limiting example a GPS tracking device, incorporated in or in communication with the patient's portable communication device 108, which can be used determine the current location 125 of the patient which is transmitted by the tracking system 124 directly to the master control system 102 such as by an internal system (i.e. system that uses a mobile phone carrier (not shown)) as the communication network or by the portable communication device 108 using its mobile phone carrier (such as VERIZON or AT&T) as the communication network (not shown). The psychosocial system software 202 then operates to use the current location 125 of the patient to verify that the patient is at a pre-set location 126 at a pre-set time 128 for scheduled desired therapeutic psychosocial activity 130, such as attending a therapy session, a self-help group meeting, or a medical appointment, taken from a list of activities 132 personalized for each patient and stored in the memory 106 of the master control system 102. As illustrated in FIGS. 3 and 4, real-time tracking information 134 is collected and transmitted to the master control system 102 and compared by the psychosocial system software 202 with the list of activities 132 and compliant requirements 136 for the activity 130 to ensure that the patient has complied with the compliant requirements 136 by attending the scheduled desired therapeutic psychosocial activity 130. In another preferred embodiment the real-time tracking information 134 that is collected and transmitted to the master control system 102 is utilized by a healthcare worker to determine if a patient is moving in the direction the pre-set location 126 but will not be on time (will not arrive at the pre-set location 126 at the pre-set time 128) and will miss all or a portion of the psychosocial activity 130. In another preferred embodiment, if a patient is unable to at arrive at the pre-set location at the pre-set time, the master control system 102 operates to determine when an alternative therapeutic psychosocial activity 130 is available and examines the patient's schedule, all of such information being stored in memory 106, and reschedules the therapeutic psychosocial activity 130 for a new pre-set time 128 (and/or pre-set location 126).

In another preferred embodiment of the invention the master control system includes analytics software 210. Collected tracking information 134 is stored in memory 106 of the master control system 102 and the amount of time the patient is at the pre-set location 137 to participate in a therapeutic psychosocial activity 130 is recorded and stored in memory 106. The amount of time that the patient is at a pre-set location 137 to participate in the therapeutic psychosocial activity 130 is then compared with the time duration of the activity 139 by the master control system 102 which then operates the analytics software 210 (FIG. 6) to determine if the patient has complied with predetermined compliant requirements 136 (for a non-limiting example, the patient attended the entire scheduled activity) that have been developed for the particular activity and patient. It should be understood that predetermined compliant requirements 136 are developed for each patient and are dependent on the particular activity (such as but not limited to attending a meeting or taking a test), the patient, patient information (information relating to the particular patient including patient mental and health histories, cause for treatment, and other such relevant information) and can include testing requirements, therapeutic psychosocial activity requirements, medication requirements, and other relevant medical treatments.

In another preferred embodiment, the tracking system 124 utilizes the imaging device 300 on the patient's portable communication device 108 to obtain an image of the surroundings 301 at a location or stream real time video 303 of the surrounds at a location to obtain tracking information 134 which is transmitted to the master control system 102. Accordingly, the tracking information 122, such as the video 303 or images 301 of the patient's location is used by the recognition software to identify the current location 125 of the patient. For an illustrative example, the video of images can show buildings, houses, structures, parks, landscapes, art works, signs, and other objects that can be used by the tracking software cooperating with the recognition software of the identification software to identify a location.

Figure 5:
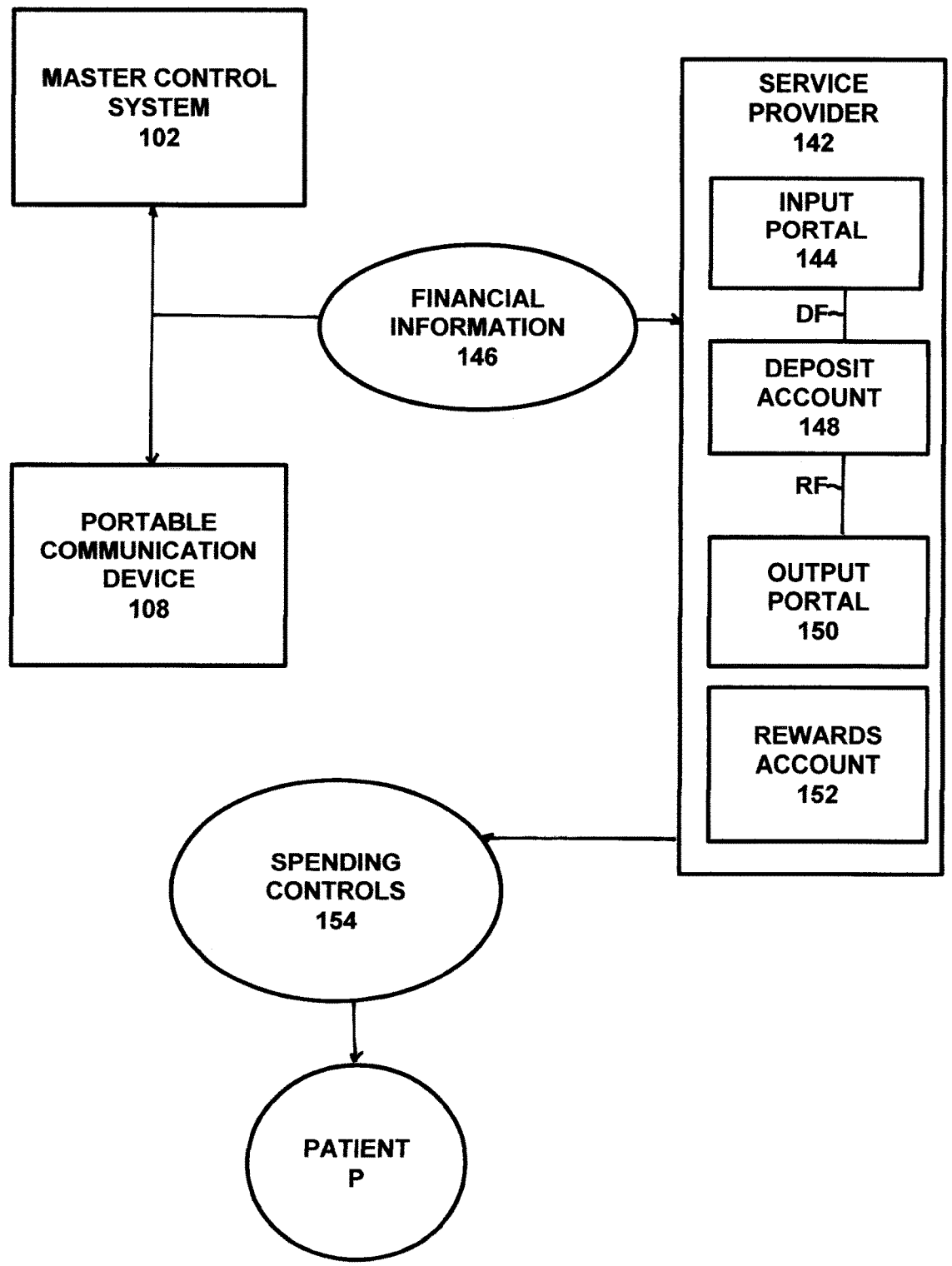
FIG. 5 is a schematic representation of a preferred embodiment of the system for encouraging therapeutic psychosocial activity showing one or more service providers including a financial service provider for receiving information for depositing funds into a deposit account, for transferring funds into a rewards account and uses spending controls that operate to limit the amount of spending or the purchases that may be made by a patient.

Service Providers:

Referring to FIG. 5, a preferred embodiment of the invention is shown whereby the master control system 102 and each portable communication device 108 are in communication with one or more service providers 142 having an input portal 144 for receiving financial information 146 for directing the depositing funds DF into a deposit (escrow) account 148 of a patient and an output portal 150 for directing a service provider 142 to transfer rewards funds RF from the deposit account 148 into a rewards account 152 of a patient. It should be understood that such service providers 142 can include various forms of service providers including, but not limited to, banking institutions, credit card providers, loyalty rewards programs, gift cards, Paypal, mobile wallet providers (e.g. Apple Wallet), and the like. In a preferred embodiment, the service providers 142 further operate to provide fine-grained spending controls 154 that function to prevent inappropriate purchases (purchasers that have been defined as being inappropriate when dealing with a user population suffering from addiction). One such service provider is the True Link reloadable prepaid debit card service (www.truelinkfinancial.com) that can function to automatically block merchants that sell drugs or tobacco to a patient.

In operation, a patient using a portable communication device or other system effective for communicating with a service provider, transmits the appropriate financial information (or funds) to a service provider which functions to obtain the funds and deposit the funds into a deposit account for a patient. For a non-limiting exemplary illustration, a patient (or a third-party) can input through the input portal of the service provider financial information in the form of debit or credit card information that the service provider uses to transfer funds from the debit or credit card provider to the deposit account. It should be understood that the deposit account is patient specific and all funds in a specific deposit account is credited to a particular patient and is under the control of the system operator. It should also be understood that as used herein the term "system operator" includes an entity or individual that is responsible for the overall operation of the system and can include, but not limited to, an individual, business entity (corporation), medical provider, therapy provider, judicial or law enforcement agency, and the like. Preferably, the system operator through the master control system 102 provides patient financial information 146 to a service provider 142 for each patient utilizing the system 100. Such patient financial information 146 can be in the form of fund withdrawal information allowing the system operator to withdraw funds from the deposit account 148.

Figure 6:
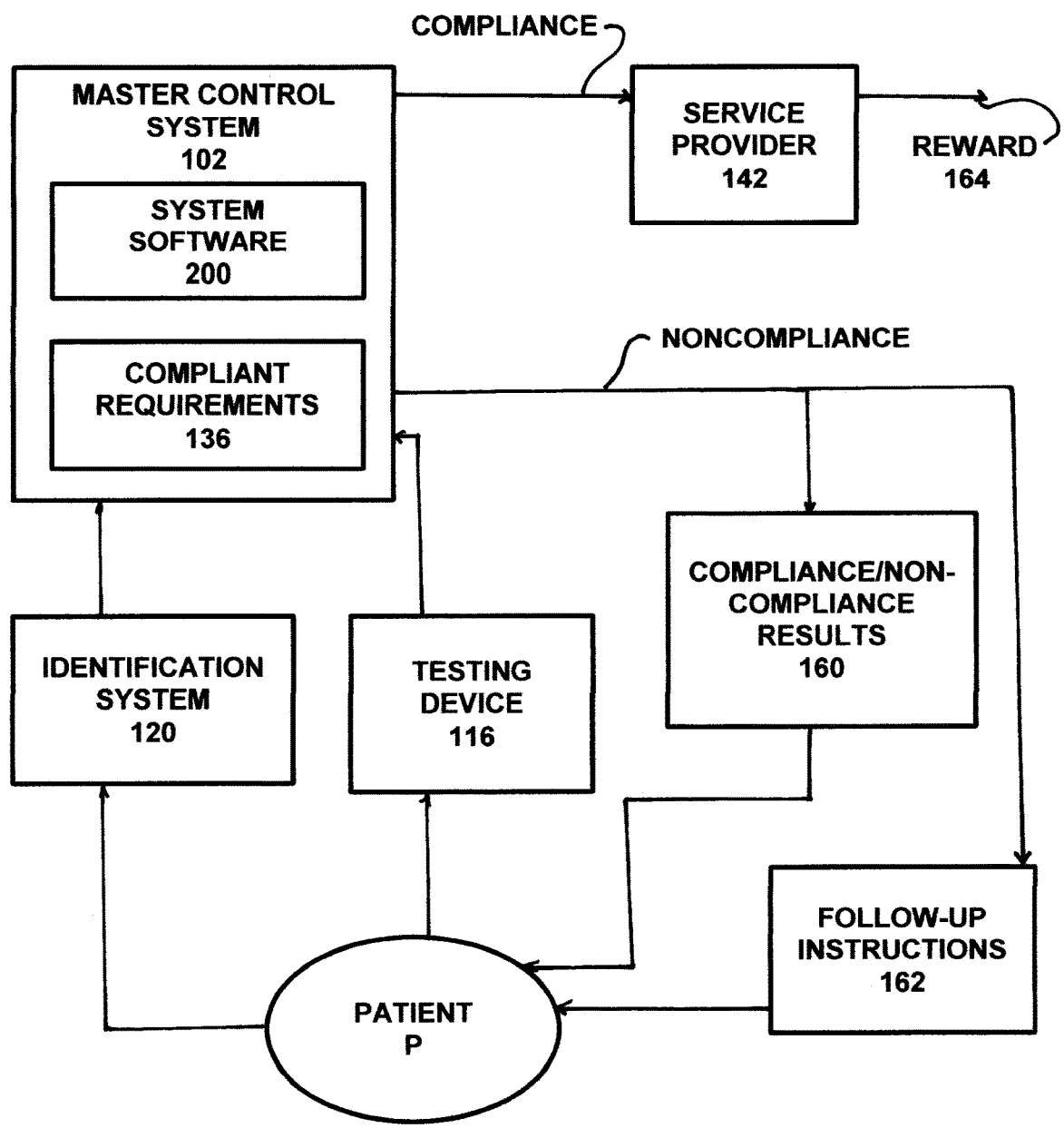
FIG. 6 is a schematic representation of the system for encouraging therapeutic psychosocial activity showing the master control system in communication with an identification system and a testing device and showing the system operating to provide a patient with a reward for meeting compliant requirements or receiving follow-up instructions when a patient is in non-compliance with the compliant requirements.

Testing and Rewards:

In a non-limiting illustration of the operation of the system, a patient P, when receiving a notice for requested information 158 (FIG. 2), randomly or by a predetermined schedule, requiring patient to perform an activity (such as using the test device 116), the portable communication device 108 and the testing device 116 operate to perform a test of the patient and collect test information 118. Preferably, during such testing, the identification software 206 functions to activate the identification system 120 which obtains identifying information 122, either immediately before being tested, while being tested, or immediately after testing, and transmits the identifying information 122 to the master control system 102. The master control system 102 operates to store the test information 118 in the memory 106 and using the psychosocial system software 202 analyzes the test information 118 to determine if the patient is in compliance with compliant requirements 136. In another non-limiting illustration when receiving a notice for requested information 158, randomly or by a predetermined schedule, requiring patient to perform participate in an activity (such as attending counseling or a therapeutic activity or meeting with a healthcare worker), the portable communication device 108 and the tracking system 124 operate to track the patient and transmit the patient's current location 125 to the master control system 102 to verify that the patient is at the pre-set location 126 at the pre-set time 128. If the patient performed the test or the activity the master control system 102 operates to transmit compliance/noncompliance results 160 to the patient's portable communication device 108 for display to the patient (FIG. 6). In the event that the patient is not in compliance, the master control system 102 operates to transmit follow-up instructions 162 to the portable communication device 108 for display to the patient. If the patient is in compliance (patient has complied with the compliant requirements 136, such as passed a drug test), the master control system 102 operates to immediately contact the service provider 142 through the input portal 144 and instructs the service provider 142 to withdraw deposit funds DF from the deposit account 148 for the patient and transfer the deposit funds DF into the rewards account 152 that functions as a reward 164 for being in compliance with the compliant requirements 136. It should be understood that rewards may also be in the form of products (goods), virtual rewards, electronic gift cards, pre-paid debit cards, or other such forms. It should also be understood that in a preferred embodiment of the invention a patient can request the form of the reward 164. It should also be understood, that the amount or value of the reward 164 can vary depending on various conditions, such as the amount of time that the patient has been in compliance, the type of activity (or testing) being done, the condition of the patient and various other conditions and criteria set by the system operator. Accordingly, the system operates to provide the patient with an instant reward thereby maximizing the effectiveness of the reward system, In a preferred embodiment, if a patient has performed certain tasks or engaged in certain social or therapeutic activities that were not assigned or requested but is deemed to be beneficial for the patient, the master control system 102 operates to immediately contact the service provider 142 through the input portal 144 and instructs the service provider 142 to withdraw deposit funds DF from the deposit account 148 for the patient and transfer the deposit funds DF into the rewards account 152 that functions as a reward 164 for being in compliance with the compliant requirements 136. Thus, encouraging the patient to engage in self-help which further enhances the patient's compliance with the program.

Figure 7:
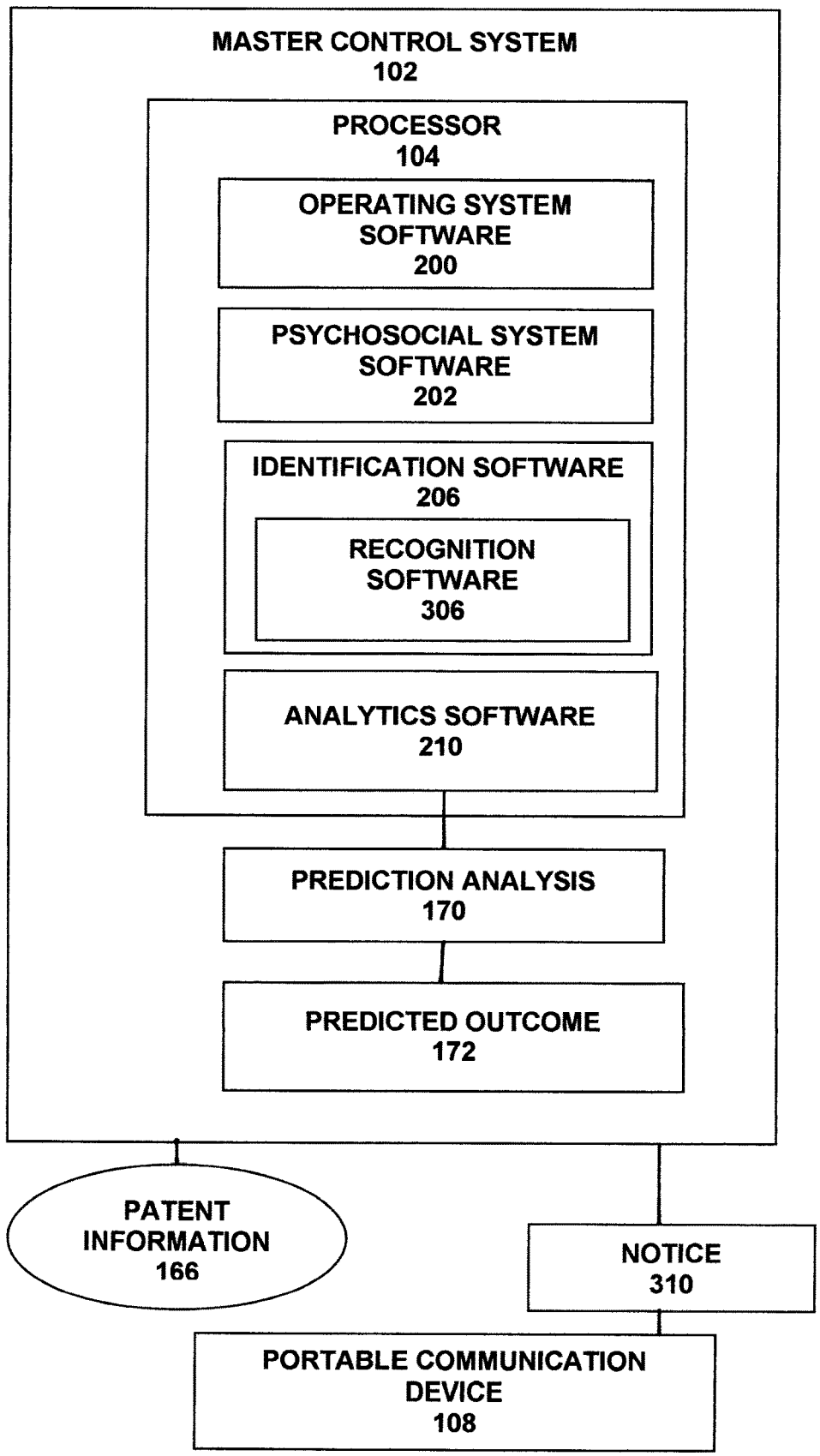
FIG. 7 is a schematic representation of a preferred embodiment of the invention showing the master control system having analytics software that operates to receive information and generate a profile and perform a prediction analysis for a patient.
Figure 8:
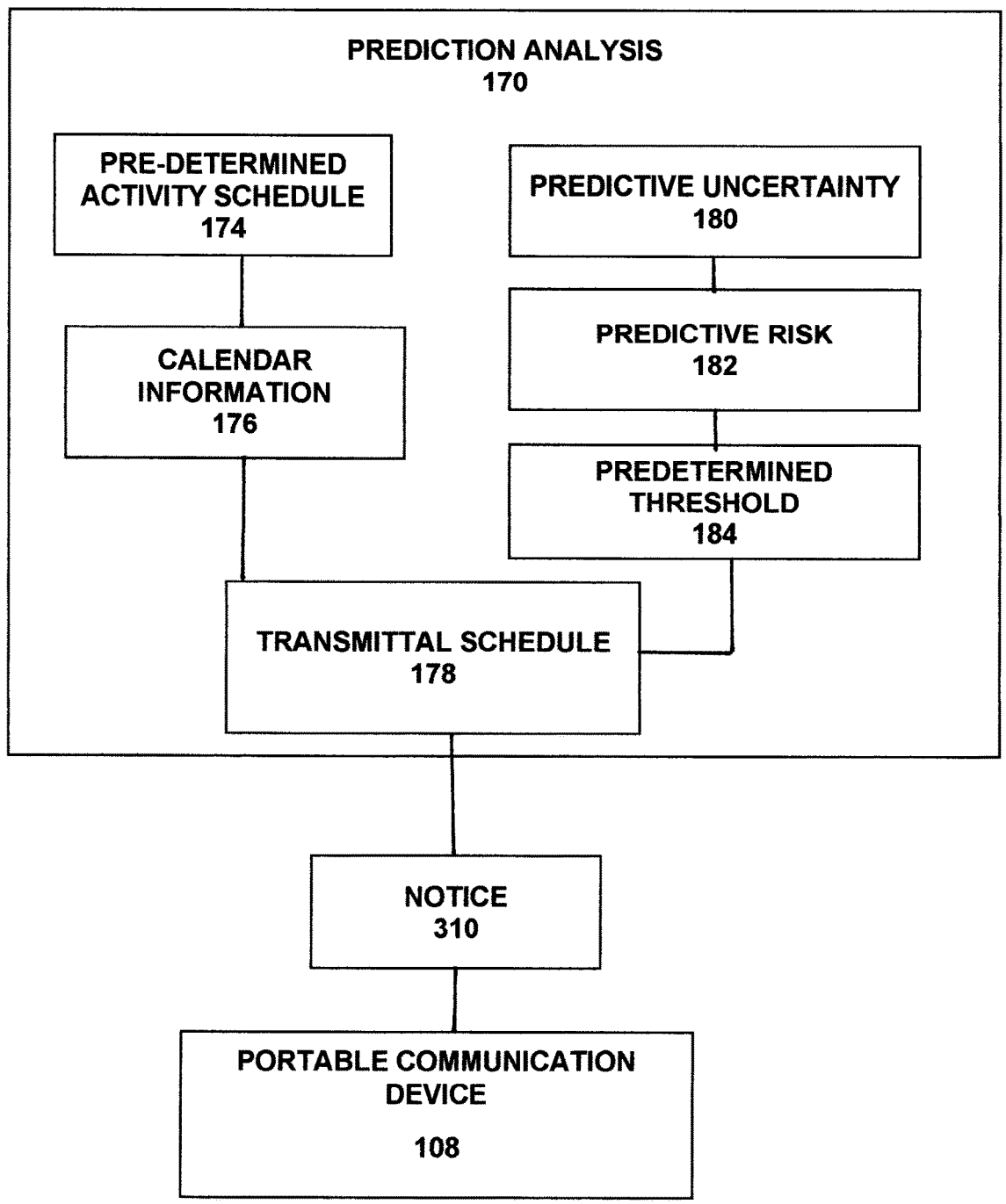
FIG. 8 is a schematic representation of the system for encouraging therapeutic psychosocial activity showing the operation of the prediction analysis and developing a schedule for testing and a schedule for sending out a notice to a patient.

Analytics:

In a preferred embodiment of the invention, as illustrated in FIG. 7, the processor 104 of the master control system 102 operates analytics software 210 that functions to receive patient information 166 and generate a patient profile 168 (such as the age and occupation of the patient, family background, education, friends, social activities and relationships, drug/tobacco/alcohol usage, etc.) and uses the generated patient profile 168 further operates to perform a prediction analysis 170 for a patient and arrive at a predicted outcome 172 that indicates the likelihood (patient is at a high risk or low risk) that the patient will continue to comply with a specific therapy and/or the likelihood that the patient will need extra testing, therapy, activities, interventions, and other predictions with respect to the patient and the patient's behavior. The predicted outcome 172 is either continuously updated or periodically updated based on the patient's behavior and changes in the environment (such as, but not limited to, events, holidays, social gatherings, patient's health, and other factors that may influence the patient). It should be understood that numerous prediction analysis methods and systems exist that create a statistical model and use predictive algorithms to create an predicted outcome that can be used to trigger early interventions before the patient violates a condition of treatment. It should also be apparent that the data feeding into the statistical model can further take into account specific patient information 166, such as but not limited to the physical location of the patient, contacts made by the patient, events taking place, nearby distractions, usage of other software and apps, spending data from the rewards account, and past behavior of the patient. Furthermore, the predicted outcome can trigger requests (notices for requested information) to be transmitted to the patient for test information (or to participate in an activity) when the predicted outcome indicates that a patient is at a predictive high risk (it is determined that it is more likely that patient will violate a condition of treatment than not violate a condition of treatment with a pre-determined amount of time) of violating a condition of treatment. If the predicted outcome indicates that the patient is at a high risk (the predicted outcome indicates that the likelihood that a patient will violate a condition requirement is greater than the likelihood that the patient will not violate a condition requirement or that the likelihood the patient will engage or participate in an activity that would be detrimental to the patient than the likelihood the patient will not participate in such an activity), such a predictive outcome can also trigger the master control system to send a request (notice for requested information) for test information (or to participate in an activity) or when the predicted outcome indicates that the patient is at low risk and fewer tests or activities can be requested or performed (the predicted outcome indicates that the patient is not likely to violate a condition of treatment). As illustrated in FIGS. 2 and 7, in a preferred embodiment of the invention the analytics software 210 operates to receive patient information166 and other information, such as test information 118 (and/or tracking information 134), and generates a patient profile 168 and preforms a real-time prediction analysis 170 for a patient. Preferably, the real-time prediction analysis 170 creates a pre-determined activity schedule 174 (to perform a test or to attend an activity) and using calendar information 176 creates a transmittal schedule 178 for transmitting one or more notices for requested information 158, such as notices for testing (or to attend an activity), and transmits the notices for requested information 158 in accordance with the transmittal schedule 178 to a patient's portable communication device 108. Preferably, predetermined activity schedule 174 and the transmittal schedule 178 are created by the analytics software 210 based on various factors including if the analytics software 210 calculates a predictive uncertainty 180 (patient's risk if violating a compliant requirement is increasing or decreasing) or a calculated predictive risk 182 (the likelihood that a patient is going to violate a compliant requirement is more likely or less likely) which reaches a predetermined threshold 184 the likelihood that a patient will violate a compliant condition is very likely). It should be understood that predetermined threshold could be a scoring based on certain factors or could simply be one or more specific factors. For example, various factors, such as specific information in the patient's profile and specific patient information, such as demographic data, consistency of the patient complying or not complying with certain assigned task or attending activities, consistency of a patient taking a requested test and passing the test, all can be given a score (or value) and if the scores add up to a certain level (predetermined threshold) the analytics software operates to modify the activity schedule, such as increasing the rate of testing. Accordingly, unlike systems that randomly requests patients to perform or take a test, the system of the subject invention operates to create a pre-determined activity schedule for testing or attending an activity based on various parameters including predictive uncertainty and predictive risk for the patient which will be automatically update as new patient information is received. It should also be understood that if a patient's predictive risk is high or certain patient information is received, such as for a non-limiting example: if the patient will be attending one or more holiday parties, the analytics software will give the specific patient information a specific score which could amend or modify the patient's predictive uncertainty or predictive risk, the pre-determined schedule will be modified for testing, such as by increasing or decreasing the number of type of test or activities being requested. In another preferred embodiment if the invention analytics software 210 operates to compare test information 118 obtained from a patient to previous test information obtained for the patient and then determines if there is any inconsistency. For a non-limiting example, if a blood sample shows the patient had a certain cholesterol level or a blood type and a follow-up test shows a significantly different cholesterol (and time and/or patient's activity would not support such a change) or the patient's blood type is not consisted, the analytics software prepares a predictive outcome 172 indicating such an inconsistency and sends a notice 308 to an operator (such as a therapist or health care worker) notifying of the inconsistency or that the predictive outcome 172 needs to be reviewed. The operator can then determine if additional testing is necessary. It should also now be understood, that in another preferred embodiment the analysis software 210 also operates to examine test results to determine if there is an inconsistency with normal or expected results, such as levels that may indicate the patient has a potential health problem, such as a problem not previously diagnosed, or a diagnosed health problem is improving or not, or that the patient may be partaking in an activity that may be detrimental to the patient's health. For a non-limiting example, the test information may include heart rate or blood pressure test information which can be used by the analysis software to make a predictive outcome that the patient may have an underlying health problem of the patient has or is performing a negative activity (such as taking a drug or smoking, etc.). The predictive outcome can then include various additional tests or tasks that should be assigned to the patient or other activities, such as an intervention, that should be performed.

In another preferred embodiment of the invention, the imaging device 300 of the patient's portable communication device operates to take the facial image 302 of the patient or operates to take a video of the patient showing the facial appearance of the patient over a period of time. The facial image 302 or video 304 is transmitted by the patient' mobile communication device 108 to the master control system 102. The master control system then uses the recognition software 306 of the identification software 206 in cooperation with the analytics software 210 to examine the facial image or video to make a predicted outcome 172. For a non-limiting illustration, the analytics software 210 uses the recognition software 306 that operates to use facial and body patterns and movements of the patient to calculate a predictive risk 182 and/or make a predicted outcome 172. For example, certain facial and body movements are known to be indicative of fatigue, enthusiasm, anxiety, and the current emotional state of a person. Accordingly, the analytics software can use such facial and/or body movements of the patient to make a predicted risk and predicted outcome for the patient that indicates the physical and/or emotional state of the patient or uses the physical and/or emotional state of the patient based on the facial and/or body patterns and movements.

Figure 9:
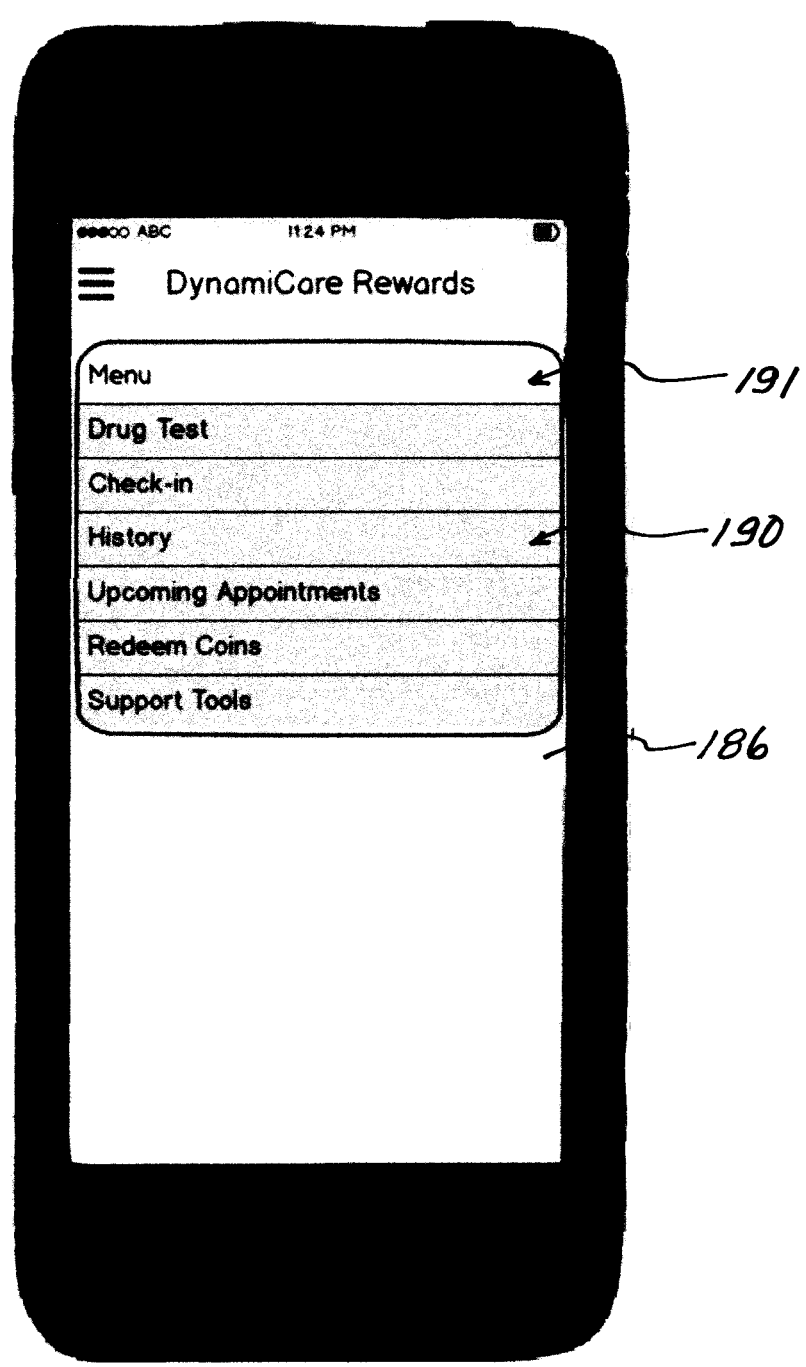
FIG. 9 is a schematic representation of a portable communication device for use by a patient having a display screen showing a menu of operations.

Non-Limiting Illustrations:

Referring to FIGS. 9-27, are schematic representations of a preferred embodiment illustrating a portable communication device for use by a patient utilizing the system and method for encouraging therapeutic psychosocial activity of the subject invention. As shown, the portable communication device 108 includes a patient output device 186 in the form of a display screen which operates to display information and includes one or more fields 190 for use by a patient in responding to a notice for requested information 158. As illustrated in FIG. 9, the system 100 operates to transmit from the master control system a menu 191 allowing the patient to select from one or more menu options (fields) 190. Preferably, the display screen is a touch screen allowing the patient to select various options (fields) 190 by simply touching the surface of the display screen using the patient's finger.

Figure 10:
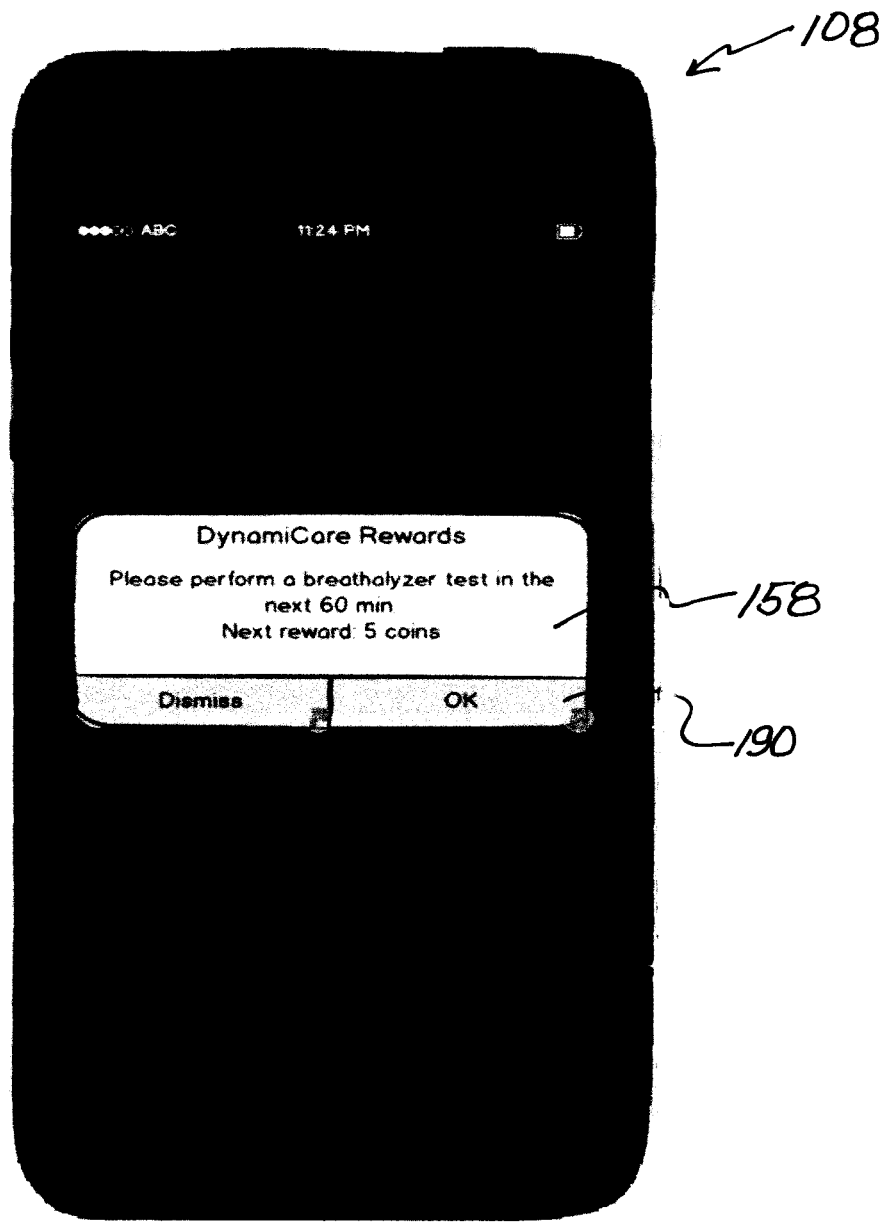
FIG. 10 is a schematic representation of a portable communication device for use by a patient having a display screen showing a notice for requested information sent to the patient and having one of more options (fields) for the patient to accept or dismiss the notice.
Figure 11:
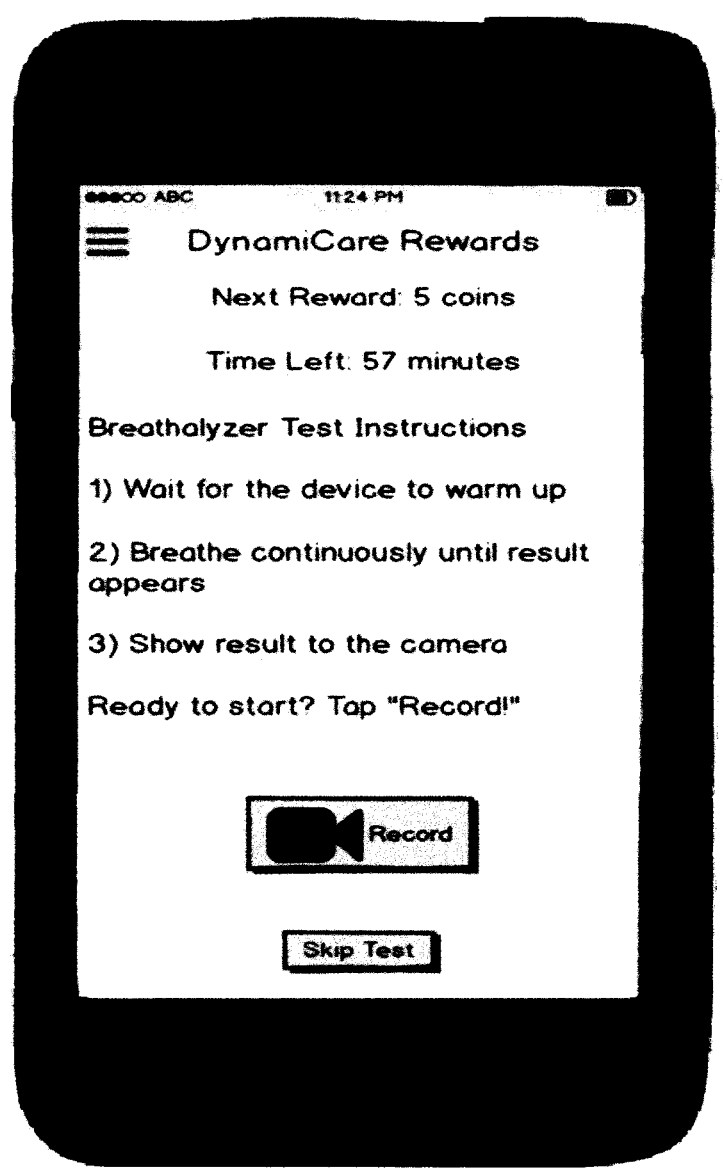
FIG. 11 is a schematic representation of a preferred embodiment of a portable communication device having a display screen for providing information to a patient for operating a testing device in response to the notice for requested information.
Figure 12:
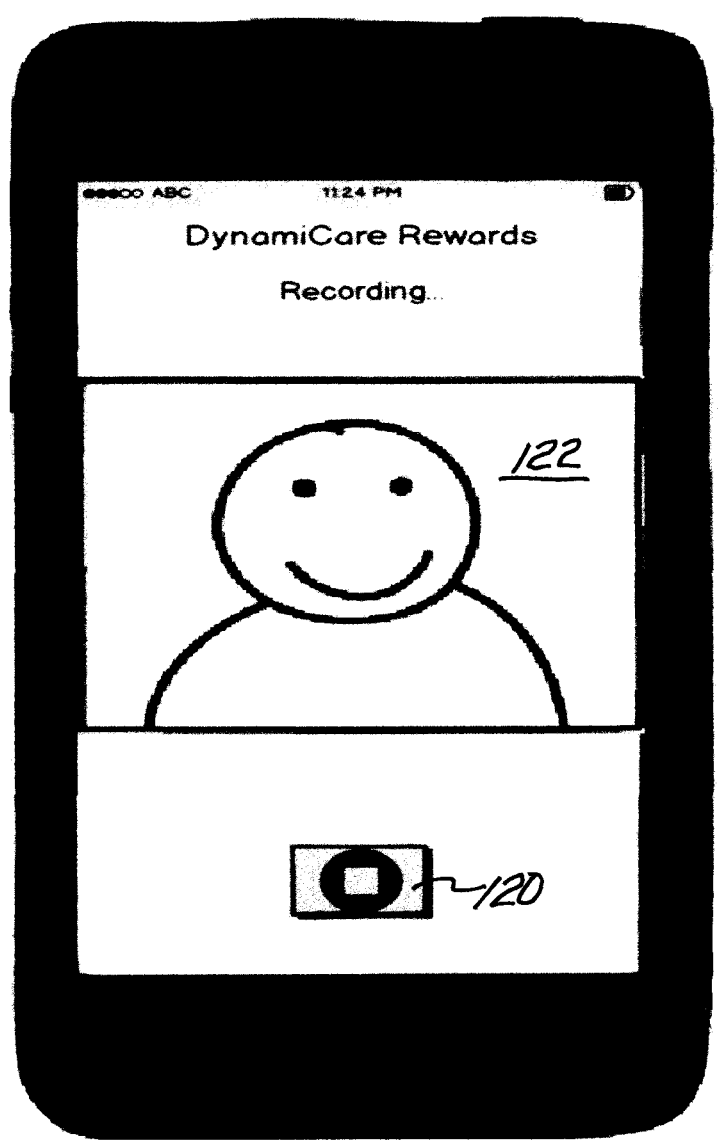
FIG. 12 is a schematic representation of a preferred embodiment of a portable communication device having a display screen and a testing device that operates to create a video of a patient and displaying the video on the display screen.
Figure 13:
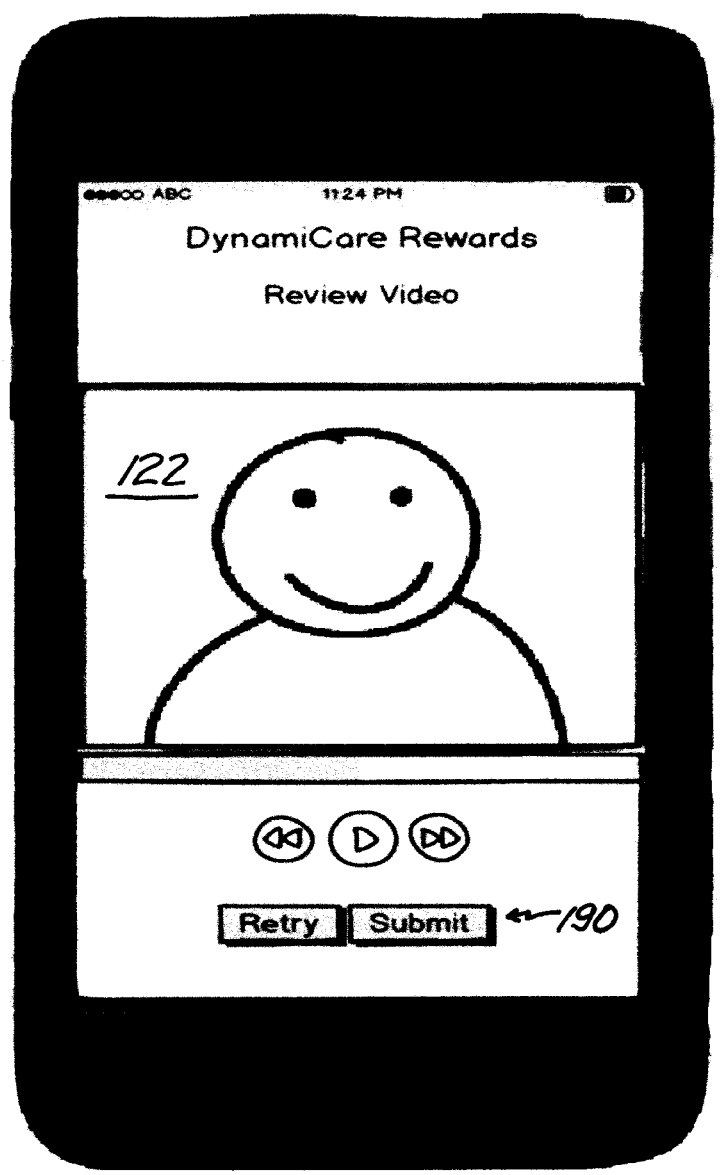
FIG. 13 is a schematic representation of a portable communication device for use by a patient having a display screen showing the video of FIG. 12 and having one or more fields allowing the patient to retake a test (create a new video) or submit test information (video) for transmission to the master control system.
Figure 14:
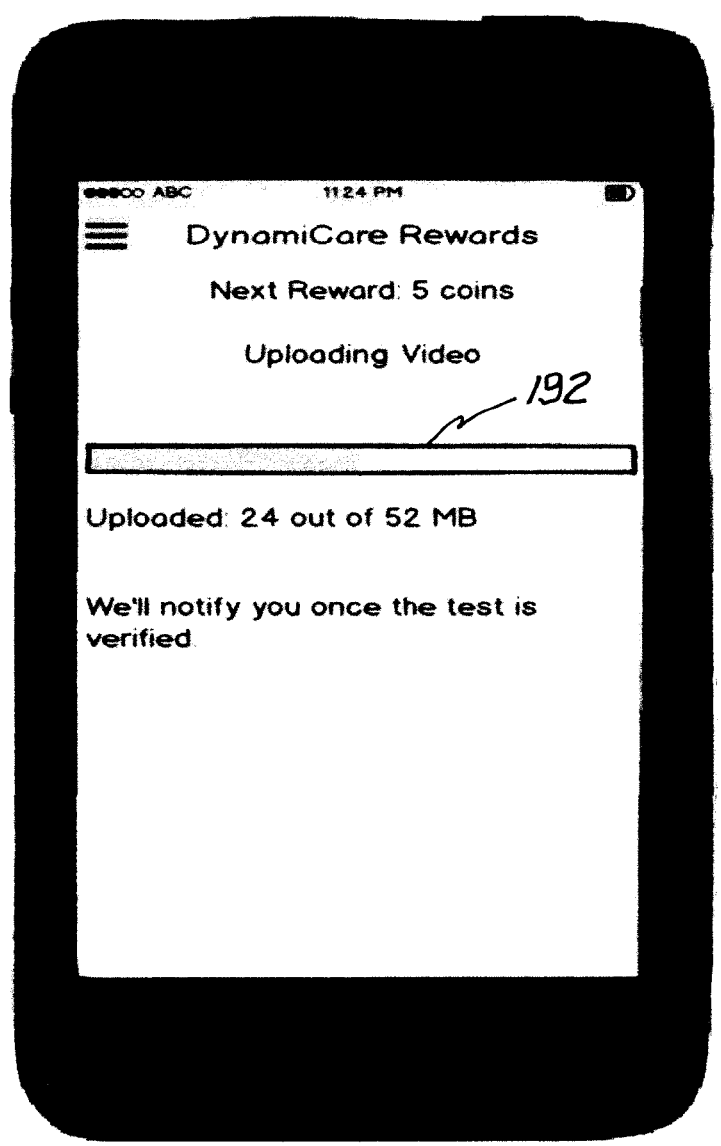
FIG. 14 is a schematic representation of a portable communication device for use by a patient with a display screen and having an indicator for showing that test information (video) was transmitted to the master control system.

In one non-limiting illustration, if the patient selects the "Drug Test" field, such as when the patient receives a notice for requested information, the system operates to display the request and the compliant requirements (FIG. 10). The patient can then select the appropriate option (field) 190 to agree to comply with the notice or not to comply and dismiss the notice. If the patient selects ("clicks") the option to accept and comply with the notice, the system software 202 operates to transmit information such as instructions for operating the testing device (FIG. 11). In a non-limiting illustration, as illustrated in FIG. 12, the display screen and the identification system 120, has an imaging device 300 which in this example in the form of a video camera, operate together to start a real-time video stream of a patient that creates identifying information 122 which is displayed on the display screen. The patient can then select to transmit the identifying information (real-time video stream) to the master control system by selecting the appropriate option (field) 190. The master control system 102 using the recognition software 306 than operates to identify the patient, such as by recognizing the face of a patient. If the identifying information 122 is not adequate (for example, the patient went out of view of the imaging device), the patient can select the appropriate option (field) to reactivate the identification system to obtain new identifying information 122 (FIG. 13). In a preferred embodiment the display screen has an indicator 192 that indicates that the test information 118 and/or identifying information 122 is being transmitted to the master control system (FIG. 14).

Figure 15:
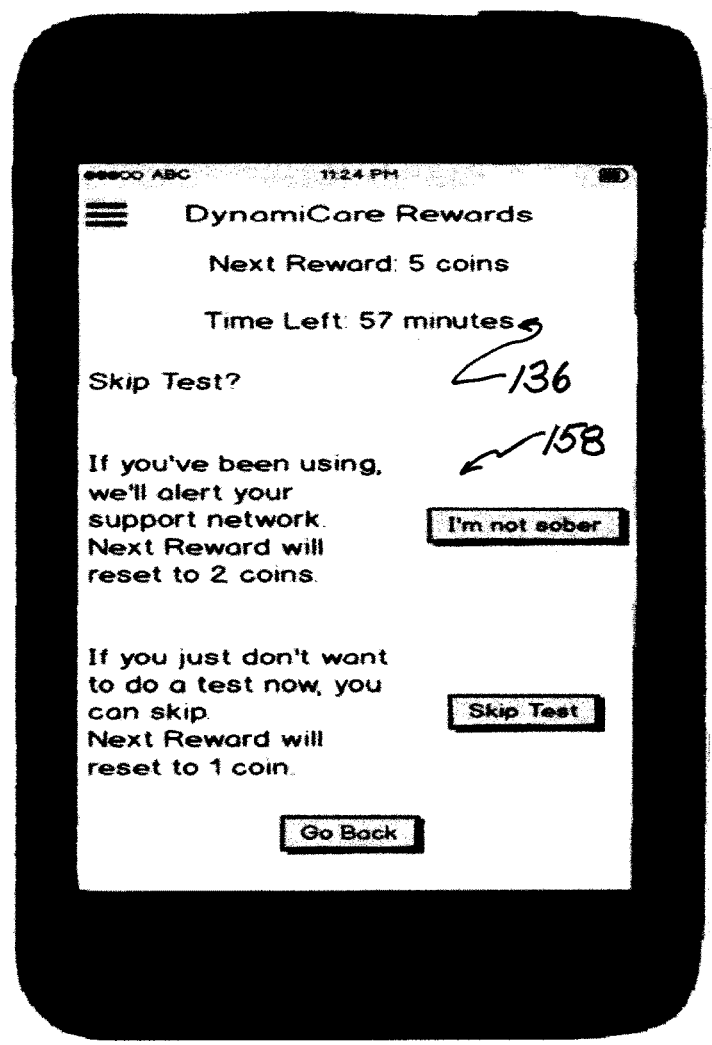
FIG. 15 is a schematic representation of a portable communication device for use by a patient having a display screen showing another notice for requested information.
Figure 16:
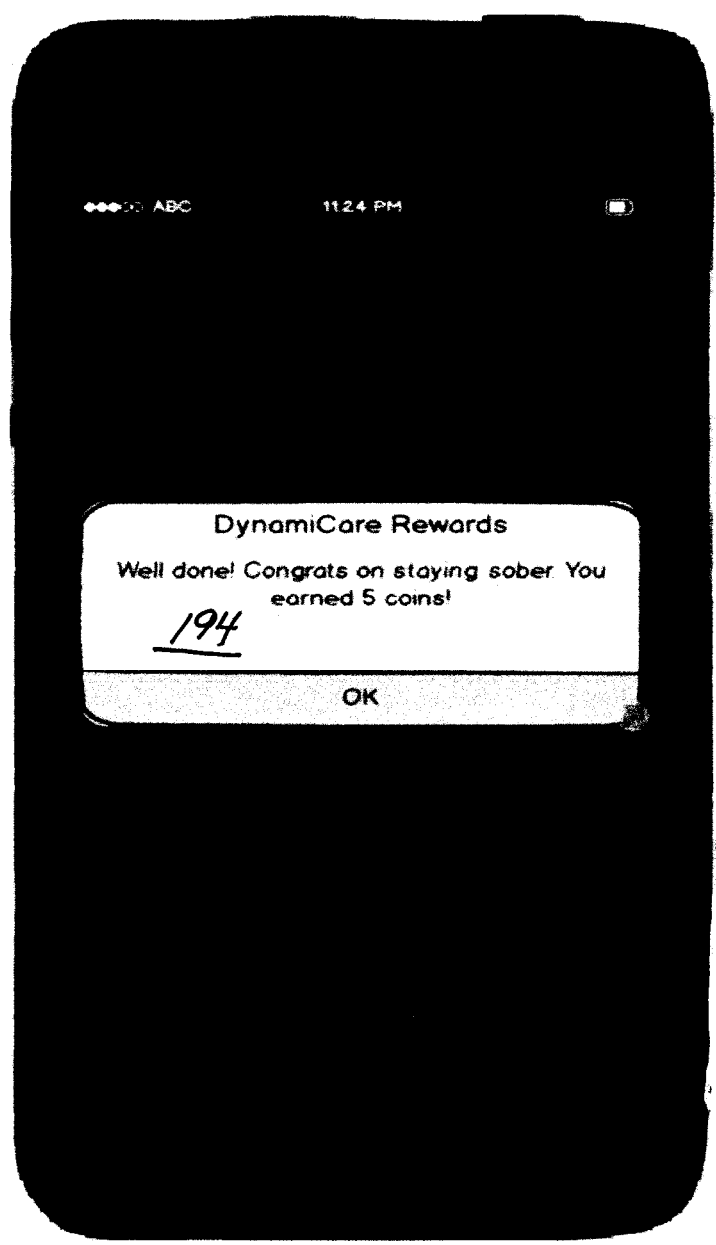
FIG. 16 is a schematic representation of a portable communication device for use by a patient having a display screen showing a verification that a reward was given to a patient for responding to a notice for requested information and being in compliance with compliant requirements.

In a preferred embodiment if the patient decides to dismiss and not to comply with the notice of requested information by selecting the appropriate option (field) 190 (FIG. 10), the portable communication device operates to communicate with the psychosocial system software 202 of the master control system 102 which operates to transmit follow-up instructions to the patient portable communication device, such as requesting the patient to indicate his/her condition (i.e. if the patient is sober). The patient can either satisfy the compliant requirements 136 by responding or can confirm that the patient does not wish to comply with the notice and take the test (FIG. 15). If the patient conforms to the compliant requirements in the notice of requested information, the system operates to send a verification notice 194 that acknowledges that the patient received the predetermine reward which was deposited in the patient's rewards account (FIG. 16).

Figure 17:
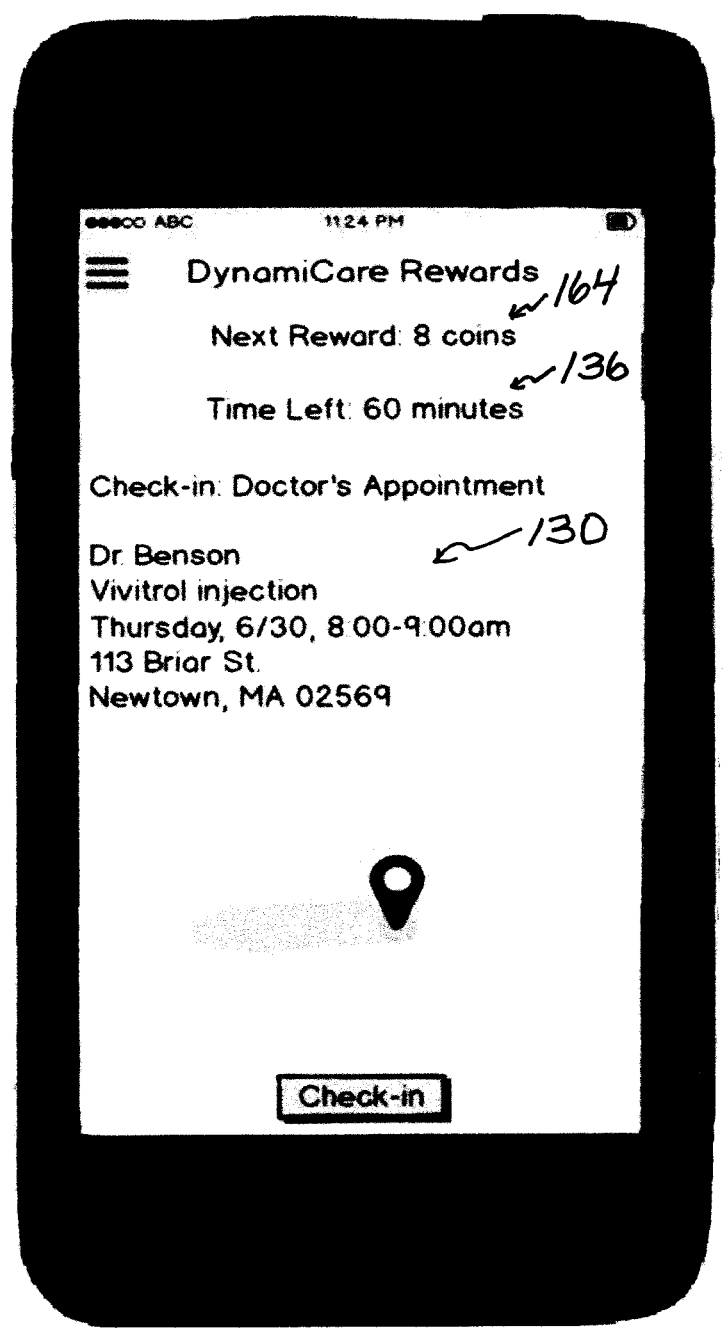
FIG. 17 is a schematic representation of a portable communication device for use by a patient having a display screen showing an activity and compliant requirements for a patient to participate and receive an award and a field for use by the patient to check in when arrived at the activity.
Figure 18:
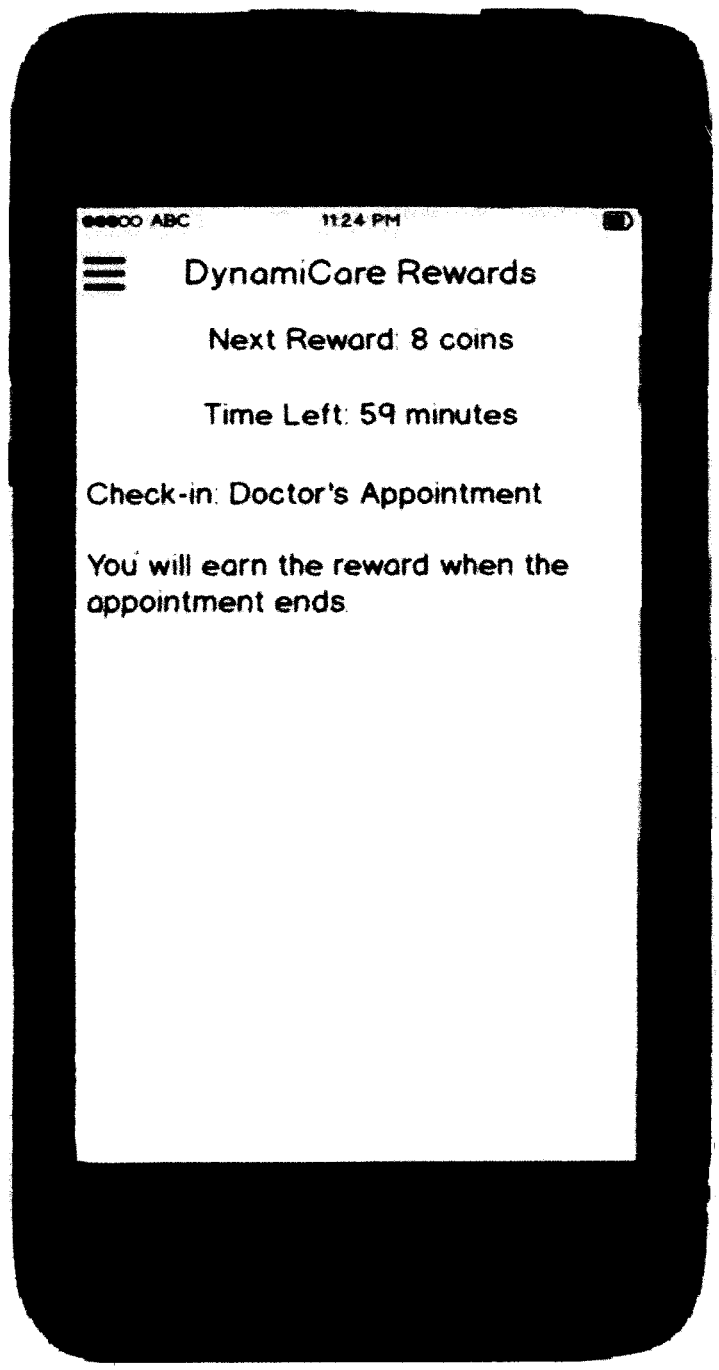
FIG. 18 is a schematic representation of a portable communication device for use by a patient having a display screen showing a reminder for the patient of an activity.

In another non-limiting illustration, the compliance requirement is a scheduled activity, such as a doctor's appointment. As shown in FIG. 17, the activity 130 is identified in the display screen and includes compliant requirements 136, such as time remaining to arrive at the pre-set location of the activity, and the amount of the reward 164 that will be awarded upon completion of the activity. Preferably, the system further operates to send reminders to the patient, such as illustrated in FIG. 18 of the activity.

Figure 19:
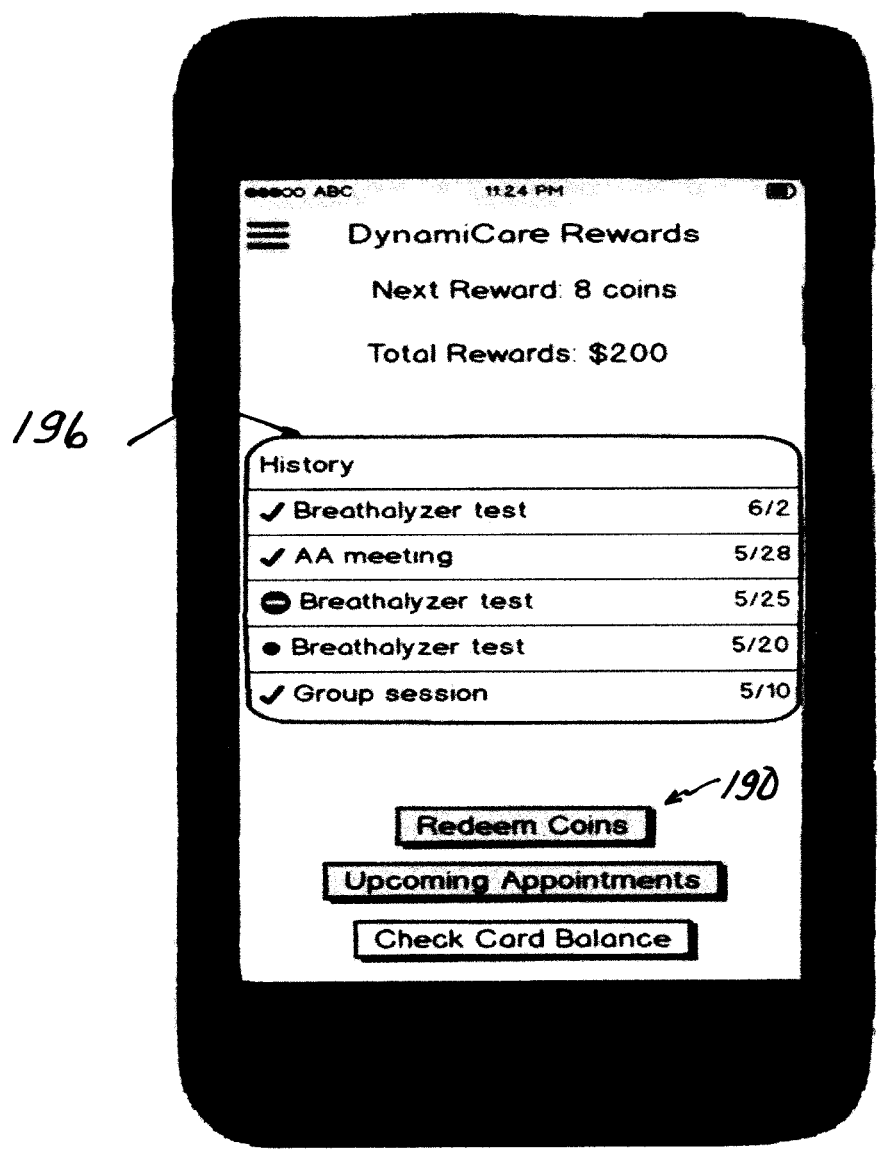
FIG. 19 is a schematic representation of the portable communication device for use by a patient having a display screen for displaying a history of tests taken by the patient and one or more options (fields) that operate to allow the patient to redeem an award, request upcoming appointments and check the balance of funds in a deposit account.
Figure 20:
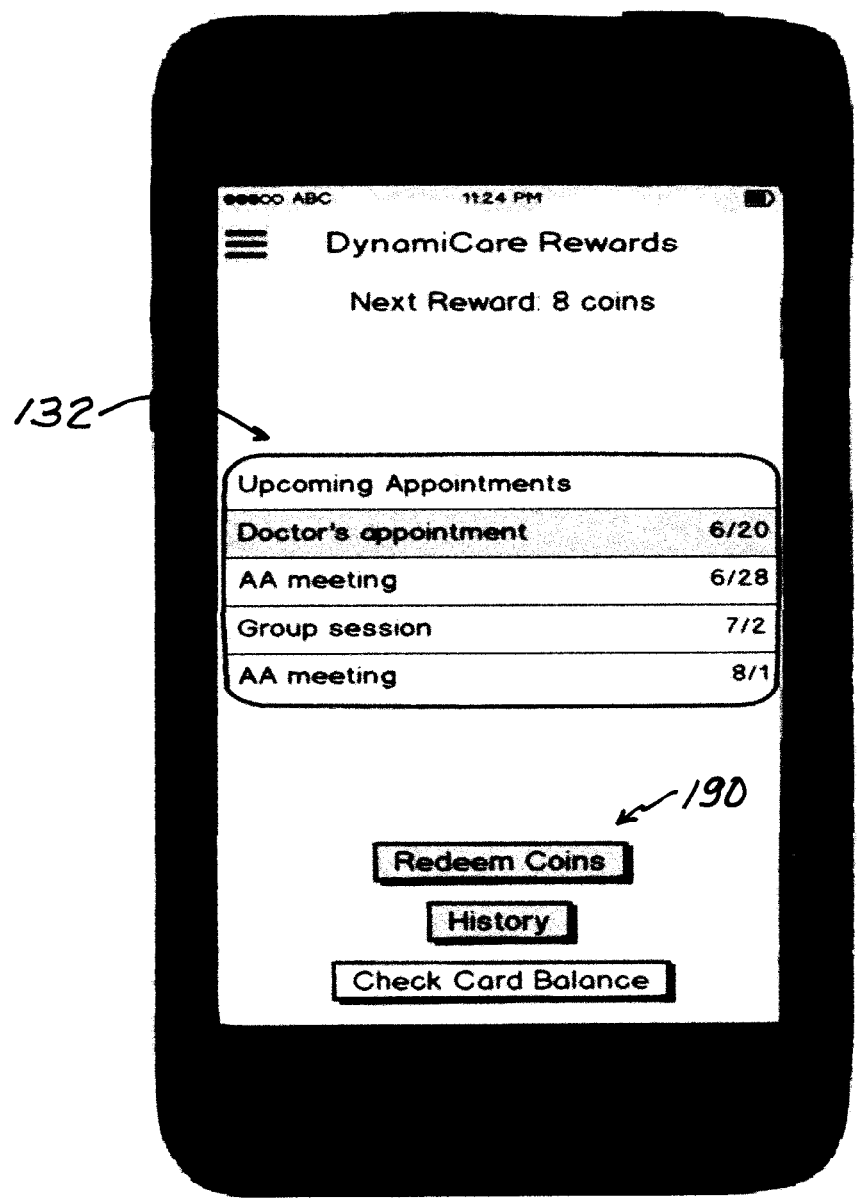
FIG. 20 is a schematic representation of the portable communication device for use by a patient having a display screen showing upcoming appointments.
Figure 21:
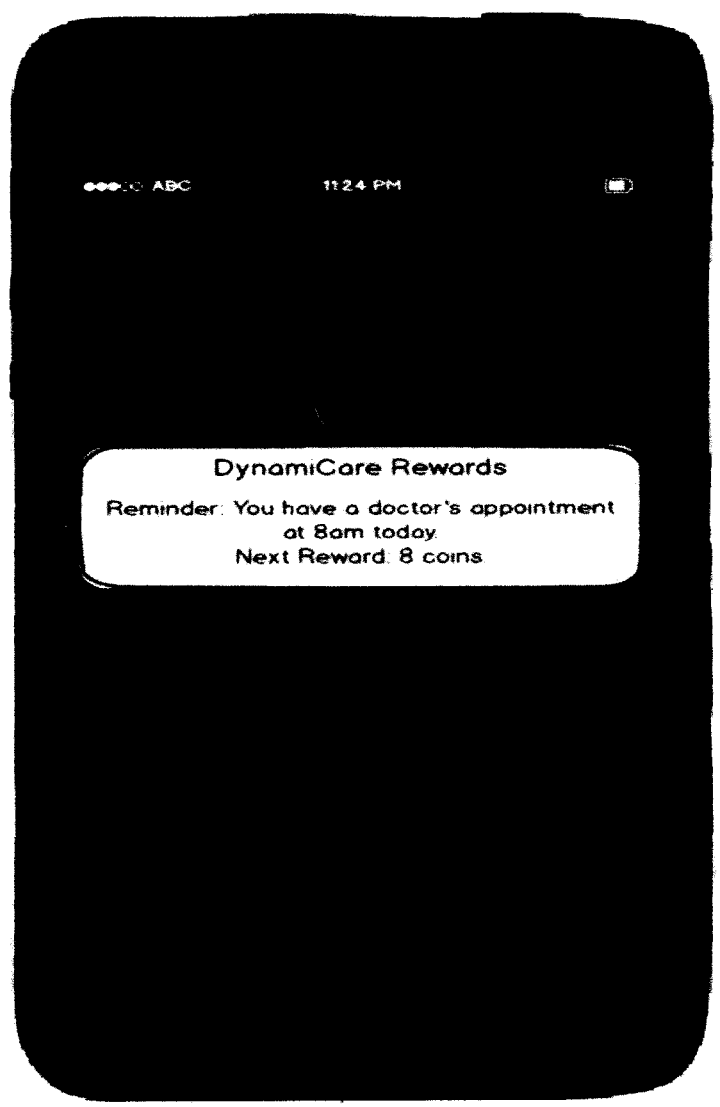
FIG. 21 is a schematic representation of a portable communication device for use by a patient having a display screen showing a reminder of an activity.
Figure 22:
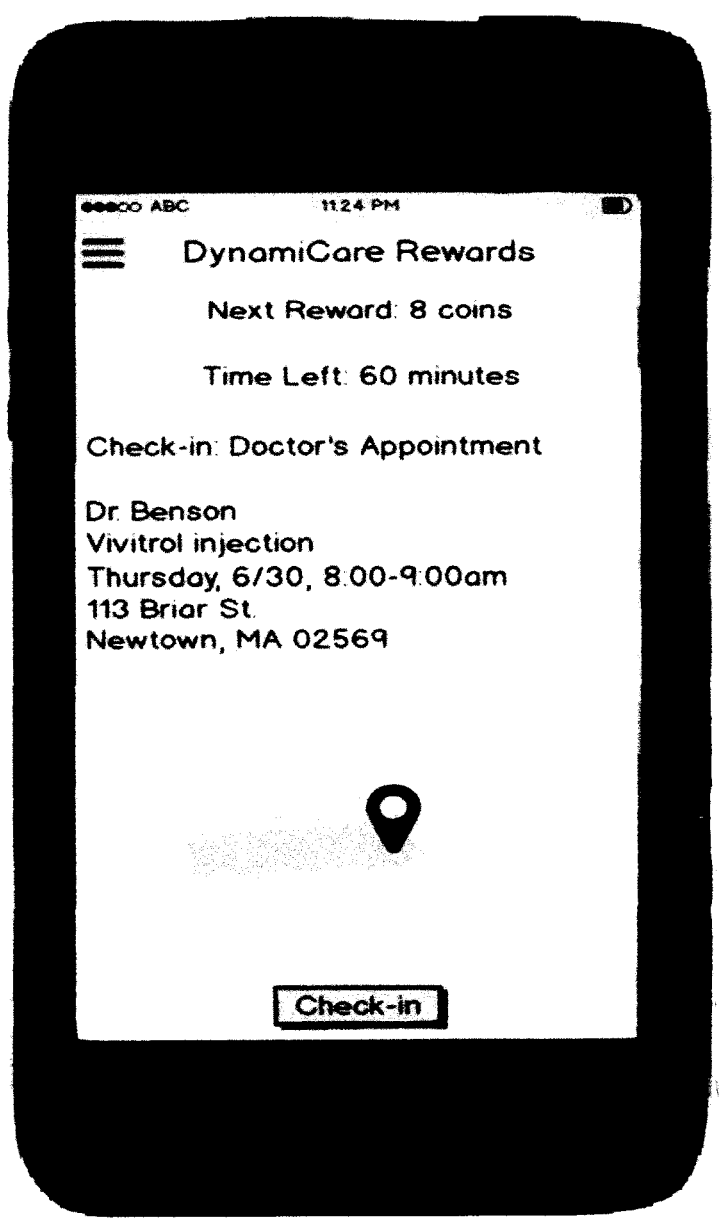
FIG. 22 is a schematic representation of a portable communication device for use by a patient having a display screen showing an activity and the amount of time remaining for a patient to complete an activity and a field for use by the patient to check in when arrived at the activity.
Figure 23:
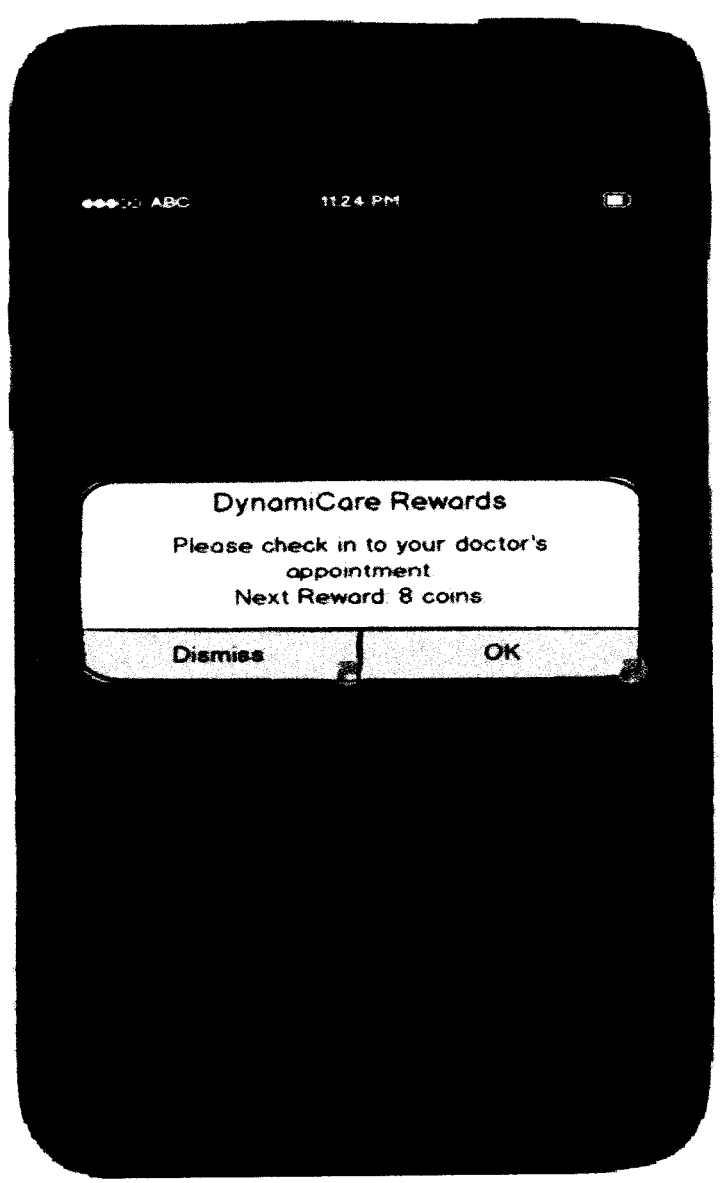
FIG. 23 is a schematic representation of a portable communication device for use by a patient having a display screen showing a reminder that a patient is to check in when arrived at the activity.
Figure 24:
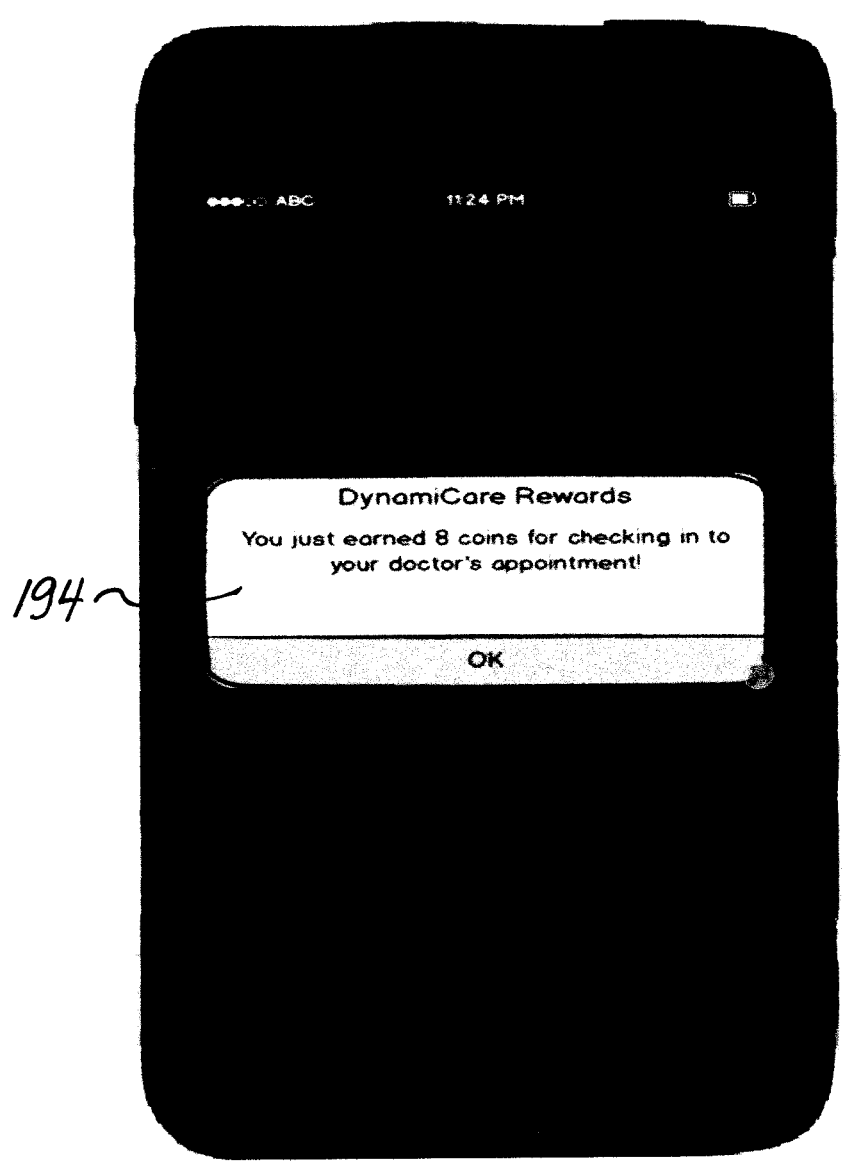
FIG. 24 is a schematic representation of a portable communication device having a display screen showing an exemplary notice illustrating that the patient has properly complied with compliant requirements and has received and is redeeming rewards.
Figure 25:
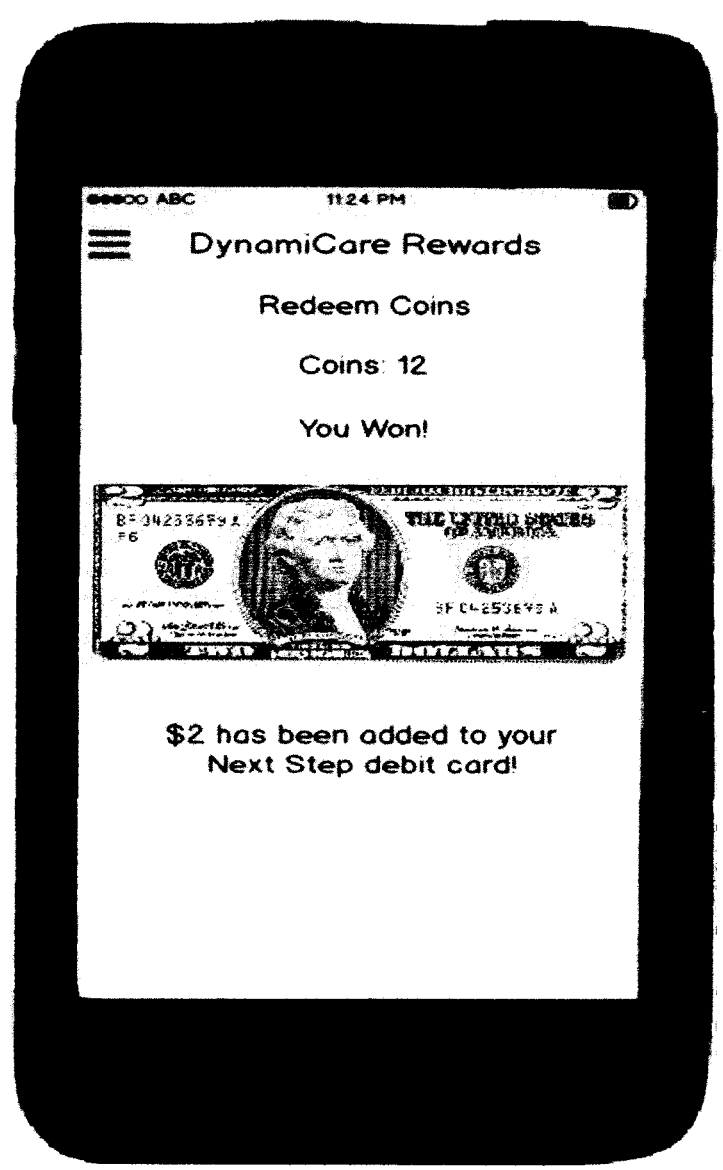
FIG. 25 is a schematic representation of a portable communication device having a display screen showing an exemplary notice illustrating that the patient has properly complied with compliant requirements and has received and has redeemed rewards and were deposited in the patient's account.

If the patient selects from the menu 191 the "history" field (FIG. 9), the system operates to display a history of test listing 196 on the display screen (FIG. 19). The system further operates to allow the patient to select various options (fields) such as to redeem a reward (coins) or to review upcoming appointments (activities) or to check on the patient's rewards account. In a non-limiting illustration, if the patient selects the "upcoming appoints" option (field), the system operates to display a listing of activities 132 scheduled for the patient (FIG. 20). In another preferred embodiment, the system operates to transmit and display on the portable communication device of a patient a reminder of an activity that the patient is scheduled to participate (FIG. 21) including details of the activity (FIG. 22). Preferably, the system provides the patient with the ability to acknowledge that the patient intends to participate in the activity and fulfill the compliant requirements or to acknowledge the patient does not intend to participate in the activity (FIG. 23). If the patient arrives at the activity and complies with the compliant requirements, the system operates to transmit a verification notice 194 of the reward 164 to the portable communication device of the patient (FIGS. 24 and 25).

The system also operates to allow a patient to select one or more options (fields) to redeem a reward, review history or testing and rewards and for checking the patient's rewards account (FIG. 20). As shown, the patient can select the option (field) for "history" which causes the system to display a history of test listing of the patient (FIG. 19) or select "upcoming appointments" (activities) field which causes the system to display a list of activities (FIG. 20) or select the "redeem coins" field.

Figure 26:
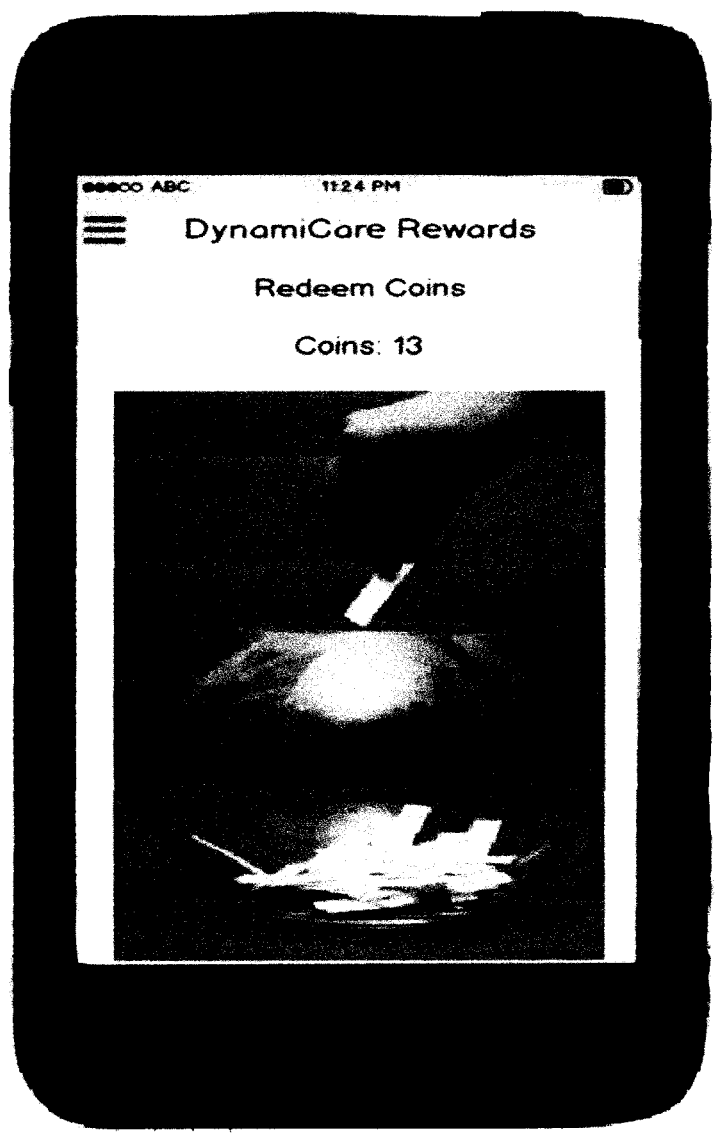
FIG. 26 is a schematic representation of the portable communication device for use by a patient having a display screen showing that the patient has redeemed a reward from the patient's rewards account.

If the patient selects the "redeem coins" option (field), the system operates to allow the patient to select or input the amount of reward the patient wishes to have transferred from the rewards account of the patient to another account, such as a bank account, PAYPal Account or other account of the patient and a verification of the transfer is transmitted to the portable communication device of the patient (FIG. 26).

In another preferred embodiment of the invention, the system further operates such that the system software 202 cooperates with the mobile operating system of a portable communication device to provide a display screen showing various conventional support tools, such as "short-cuts" that can be selected by a patient to make telephone calls to counselors, health care and emergency resources, health care motivational material and other such operations.

Figure 27:
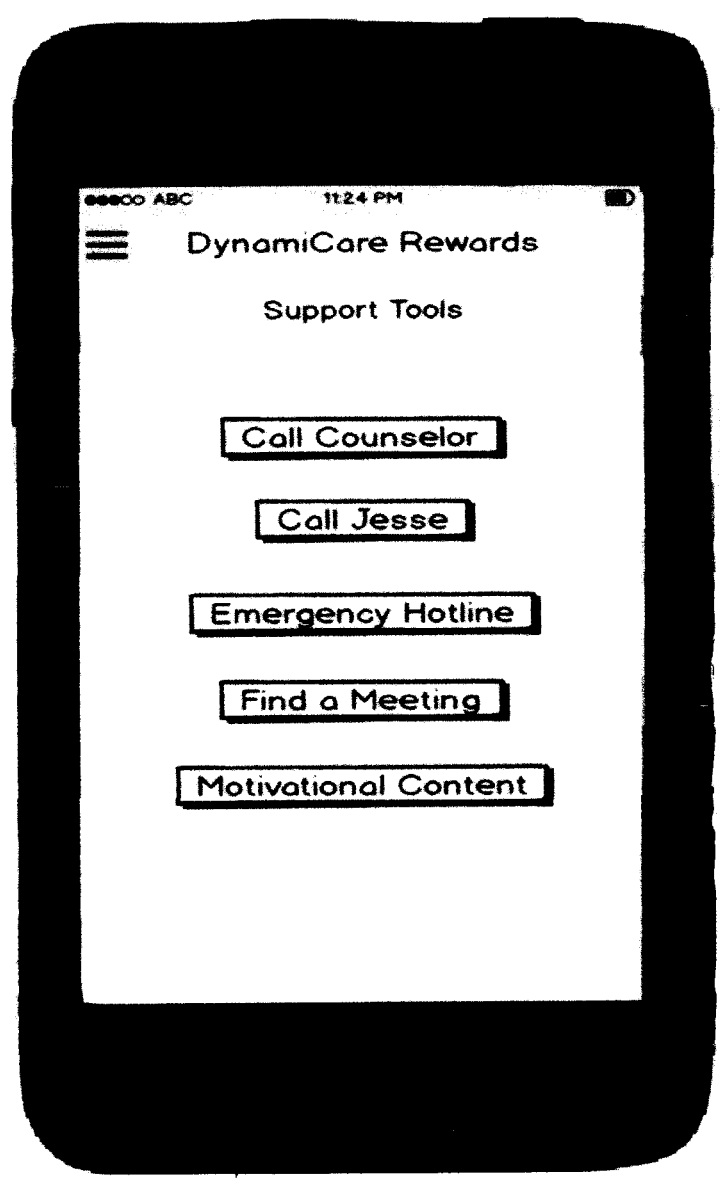
FIG. 27 is a schematic representation of the portable communication device for use by a patient having a display screen showing a preferred embodiment of the invention having fields for allowing a patient to obtain certain information, such as a meeting location, or various phone numbers (shortcuts) and other useful operations.
Figure 28:
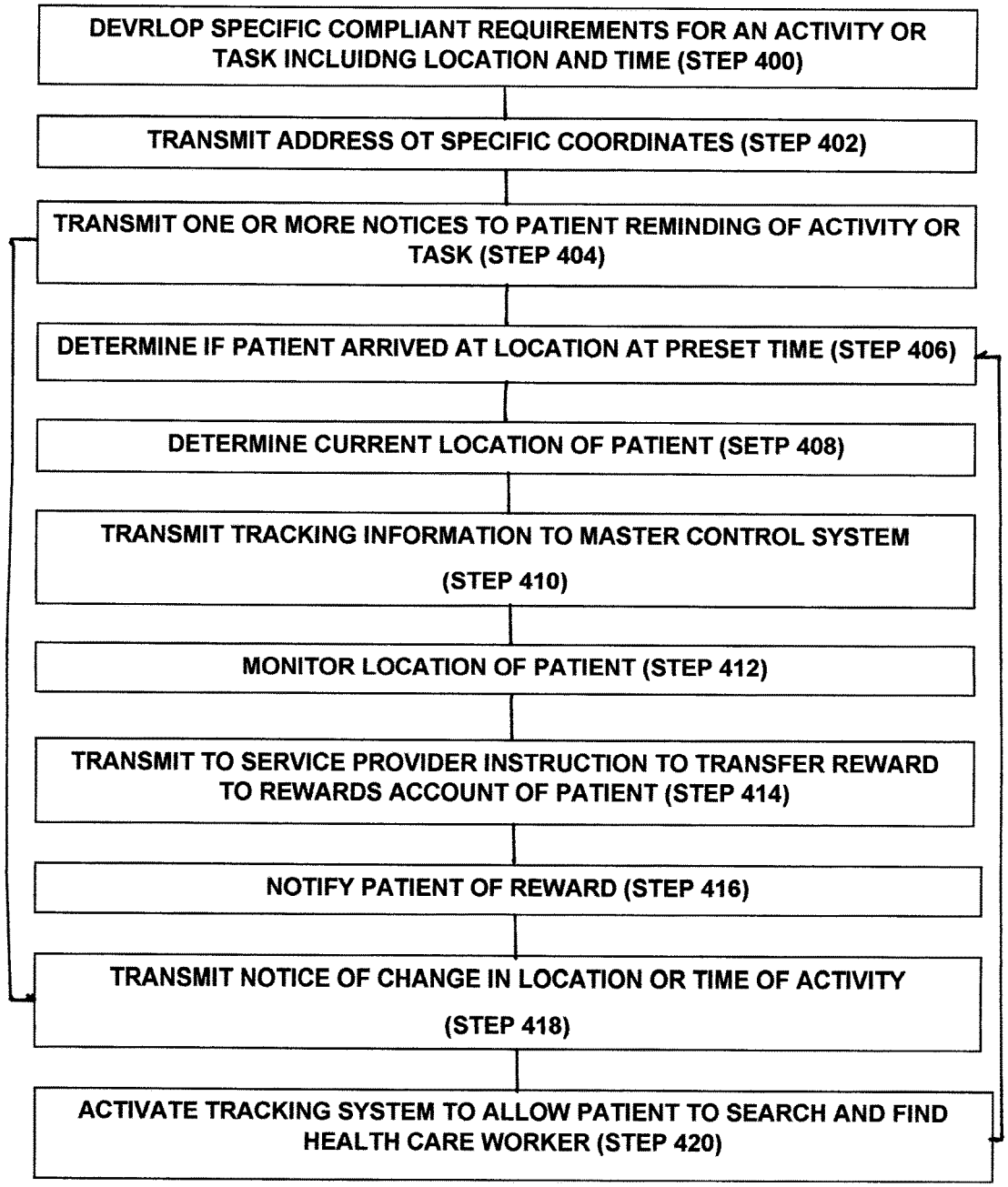
FIG. 28 illustrates the methodology of operation of a preferred embodiment utilizing the various components of the system for encouraging therapeutic psychosocial activity.

It should now be apparent that the subject invention operates to provide a treatment protocol, such as, but not limited to, for substance abuse treatment, whereby a patient is scheduled for and monitored and encourages to attend activities (for example appointments) that the patient must attend for treatment. Attendance at these activities increases the likelihood of the patient benefitting from the treatment (for example the likelihood of sobriety). Because attendance at these activities in the past has often been difficult for patients, the subject invention operates to track and verify that the patient has indeed attended the activity, for the required duration, and a reward (or a suspension of a reward) is immediately provided. Referring to FIG. 27, which illustrates the methodology and operation of a preferred embodiment utilizing the various components of the system for encouraging therapeutic psychosocial activity, the system operates such that a schedule of activities is developed which includes specific compliant requirements (such as for example a specific time, duration, and location of an activity or a specific test to be taken by the patient) (step 400). In a preferred embodiment, in the event of an activity (or test) to be held at a specific location, the system software operates to take the address and translate it into specific latitude and longitude coordinates (such as by use of GOOGLE GEOCODING service application) and stores the coordinates in the memory of the master control system for use comparison with tracking information (step 402). It should be understood that in another preferred embodiment the system software operates to provide a map of the address that can be used to precisely identify the location of the activity which can be transmitted to the portable communication device of the patient. Using a transmittal schedule created by the system software for the patient, the system operates to transmit to the patient one or more notices of requested information to the portable communication device of the patient requesting test information (such as requesting the patient to take a test or participate in an activity) and reminding the patient of the activity (or test to be performed) that the patient is schedule to participate (step 404). The master control system further operates, such as in cooperation with the tracking system, to determine if the patient has participated in the activity (such as taking the requested test or attending an appointment passively (without intervention) and complied with the compliance requirements of the activity (such as taking a test) (step 406). In a preferred embodiment, the tracking system (such as a GPS system incorporated in the portable communication device) is activated by the mobile operating system of the portable communication device upon receiving instructions transmitted by the system software, which operates to transmit the current location of the patient to the master control system (step 408). When the patient has arrived at the activity (pre-set location) at the pre-set time (or just prior to the pre-set time), the system operates to transmit the tracking information to the master control system, such as in response to the patient directing the mobile operating system to send the tracking information to the master control system or automatically (without such user intervention) (step 410). The system further operates to monitor the location of the patient until the scheduled end of the activity (step 412). It should be understood that other methods can be used to verify that a patient has attended and remained for the entire activity, such as, but not limited to the health care worker directing transmitting location information to the master control system, such as by sending the information by way of a SMS message or by "clicking" on a link sent in the SMS to confirm that the patient has fulfilled the compliant requirements of the activity. If the patient has complied with the compliant requirements for the activity, the system operates to transmit to a service provider that a reward should be immediately transferred from the patient deposit account to the patient rewards account for that specific patient (step 414) and notifies the patient (step 416).

In another preferred embodiment of the invention, if the pre-set location of the activity changes or is not defined, the system operates to send a notice to the portable communication device of the patient and to the communication device of the heath care worker participating in the activity (not shown) (step 418) and directs the mobile operating system of the portable communication device to activate a proximity sensor of the portable communication device (a short range communication protocol, such as BLUETOOTH) that allows the patient to search for the health care provider (step 420). It should be understood that the heath care worker can have a similar system that allows the health care worker to search for the patient.

It should now be apparent that the scheduled activity can include various activities including physical exercise. It is known that physical exercise can be used to improve the ability of a patient to recover from certain addictions (such as substance abuse). Using the tracking system of the system, a patient's activity, such as the amount of walking by the patient, can be monitored. Further, the system can operate to track the current location of a patient and the time spent at a location, and transmit the information to the master control system which operates the system software to determine if the location is a critical or suspect location (a location known for inappropriate activity, such as drug dealing, liquor establishments, and the like) and stores the information in the memory. This tracking information can then be used by the analytics software to calculate a predictive uncertainty or a predictive risk in developing a pre-determined scheduling for activities (such as drug testing) as well as used to allow a health care worker to provide real time intervention with the patient thereby reducing the risk that a patient will have a set-back in his/her therapy.

It should now be apparent that the system and method for encouraging therapeutic psychosocial activity of the subject invention provides a new and novel advancement in Contingency Management (CM) methodology for addition. Patients can download software (Apps.) on their portable communication device(s), as well as a testing device for proving compliance (i.e. abstinence) with compliant requirements and can interact with a reloadable store of value (rewards account) providing financial incentives. Individuals (payers, patients, family) place funds into a deposit account which the patient earns back by participating in activities of a treatment program and complying with the activity compliant requirements. The system further operates to prompt (provide notices) the patient at appropriate times to take participate in an activity (take a test) and using the identification system to prevent cheating, transmits test information (results) to the master control system for analysis. Compliance (when a patient fulfills compliant requirements such as having negative drug test results) allows the patient to receive real-time immediate rewards transferred into the patient's rewards account for immediate use by the patient. In a preferred embodiment, the amount of the rewards can be incrementally increased or variably increased. It should be understood that rewards can also be given for participation in an activity (i.e. showing up on time for an appointment or for treatment) or for adhering to medication schedules. It should also now be apparent that operators can send notices, such as dates, times, and locations of therapy or medication appointments which can be displayed to the patient on the patient's portable communication device. It should also be apparent that tracking systems, such as the GPS system incorporated in the portable communication device, can be used to track the location of the patient and to ensure the patient is at a scheduled appointment (pre-set location at a pre-set time).

It should also now be apparent that test information from drug testing, debit card spending, patient smartphone usage data (such as GPS location and call history), electronic health records, and partnering apps and products (such as group support apps or smart pill dispensers) can be inputted into the system and utilized by the analytics software, which provides families, care providers, and payers with real-time predictive analytics to create predictive outcomes and alerts indicating which patients are at highest risk for acute relapse or hospitalization within an impending timeframe (e.g., 48-hours). Such predictive outcomes facilitate timely treatment team outreach to a patient at risk, even after the acute treatment phase when the patient is remote with infrequent contact and observation. Furthermore, such predictive outcomes are used to determine a schedule for testing, so that a patient receives notices to perform a test (such as a drug test) or attend an activity (such as an appointment with a healthcare worker) at optimal times when the patient is at a high risk of noncompliance with the program. This obviates the need for a frequent, consistent testing schedule (e.g. twice per day) in a way that no existing computerized CM program is able to do.

Accordingly, it should now be apparent that the system for encouraging therapeutic psychosocial activity provides a no effort system for the operator (provider) (i.e. operators do not need to administer tests, calculate reward schedules, or distribute rewards to patients). Further the system eliminates the need for provider training in CM techniques and the burden of program administration. Predictive analytics using information obtained by the system (spending patterns, test results, etc.) and other sources, eliminates the need for frequent, explicitly specified testing schedules for CM, and provide a better result than that obtained by simple random drug testing. By predicting the times when a patient is most likely to use and sending real-time notices for patients to participate in an activity (take tests), the system allows for less frequent testing (e.g. twice per week instead of twice per day) and lowers the cost (because of fewer video verifications and less usage/depreciation of drug testing equipment) and increases the program's effectiveness.

It should also now be apparent that the system for encouraging therapeutic psychosocial activity of the subject invention is a fully automated system which in a preferred embodiment randomly assigns users various rewards systems (e.g. one with straight rewards and another with variable prize rewards). Accordingly, this enables operators to develop improved programs by allowing the gathering of knowledge in a relatively short amount of time, is relatively low cost and provides relatively quick results, because the wealth of data that is collected through the system, combined with its predictive power, gives operators an early detector of whether patients are becoming more likely to relapse without having to wait for relapse to actually happen. By analyzing information and prediction outcomes, activity schedules (such as for testing frequency, time of day/week or types of activities), types of behaviors being rewarded (therapy, medication), reward schedules (increasing rewards, randomly variable prizes), and motivational messaging can be examined and modified to improve results. By shortening the time and cost of figuring out which method works for a patient, one can rapidly iterate on the CM methodology and build a more effective intervention.

The invention claimed is:

1. A system for encouraging therapeutic psychosocial activity of a patient for changing a habit or a certain behavior of the patient, the system comprising:

a master control system that operates to transmit one or more notices for test information to a portable communication device used by the patient which then operates to inform the patient that test information has been requested, wherein said portable communication device is in communication with said master control system through a communication network;

a testing device in communication with said portable communication device and cooperates with the patient to perform a test and obtain said test information;

an identification system that operates to obtain identification information of the patient at a time the patient performs said test; and a tracking system that operates to determine the location of the patient at the time the patient performs said test;

wherein said portable communication device operates to transmit test information and identification information to said master control system;

wherein said master control system includes identification software that operates to verify the identity of the patient and analytics software that operates to use said test information to create a predicted outcome that indicates a risk of the patient is likely to violate a condition of treatment;

wherein said one or more notices for test information are transmitted to said portable communication device on a random and on a predetermined schedule and wherein said analytics software operates to automatically increase or decrease the number of said one or more notices for said test information to be transmitted by said master control system to said portable communication device based on said predicted outcome and said risk of the patient is likely to violate said condition of treatment; and wherein said analytics software further operates to automatically compare test information obtained from a patient to previous test information obtained from the patient and then determines if there is any inconsistency with normal or expected results indicating the patient has a potential previously undiagnosed health problem.

2. A system for encouraging therapeutic psychosocial activity of the patient of claim 1 wherein said one or more notices for said test information includes a time period informing the patient when said test information is to be transmitted to said master control system.

3. A system for encouraging therapeutic psychosocial activity of the patient of claim 1 wherein said identification system having an imaging device that operates with said portable communication device to stream real time video to said master control system and wherein said master control system has recognition software that operates to identify the patient and further operates to determine if the patient at any time while using said testing device to obtain said test information was out of view of said imaging device, and wherein if said recognition software determines that the patient was out if view of said imaging device at any time while using said testing device, said master control system then operates to send a notice to said portable communication device that the patient that a test must be retaken using said testing device.

4. A system for encouraging therapeutic psychosocial activity of the patient of claim 1 further comprising an identification system having an imaging device that operates with said portable communication device to stream real time video to said master control system and wherein said master control system has recognition software that operates to identify the patient and further operates to determine if a requested test and the patient at any time while taking said requested test was out of view of said imaging device, and wherein if said recognition software determines that said requested test or the patient was out if view of said imaging device at any time while taking said requested test, said master control system then operates to send a notice to said portable communication device of the patient that said requested test must be retaken.

5. The system for encouraging therapeutic psychosocial activity of the patient of claim 1 wherein said master control system operates to transmit one or more notices for the patient to attend a therapeutic psychosocial activity at a preset location and at a preset time and wherein said master control system operates to use said tracking information to determine a current location of the patient and to determine if the patient will be at said preset location at said preset time, and if said master control system determines that the patient will not be at said preset location at said preset time, said master control system operates to find an alternative therapeutic psychosocial activity and examines a schedule for the patient and reschedules said therapeutic psychosocial activity based on said available alternative therapeutic psychosocial activity and said schedule for the patient.

6. The system for encouraging therapeutic psychosocial activity of the patient of claim 1 wherein said imaging device takes images or a video of the patient and wherein said master control system operates to use said images or said video to make a predicted outcome that indicates the physical and/or emotional state of the patient.

7. The system for encouraging therapeutic psychosocial activity of the patient of claim 1 wherein said testing device provides a digital quiz designed to test the understanding of the patient of therapeutic activities.

8. The system for encouraging therapeutic psychosocial activity of the patient of claim 1, wherein said testing device provides a digital survey that the patient can periodically complete and designed to collect clinically relevant information about the patient.

9. The system for encouraging therapeutic psychosocial activity of the patient of claim 1 wherein said master control system further transmits to said portable communication device a request that the patient participate in a therapeutic psychosocial activity at a pre-set location and at a pre-set time and wherein said portable communication device further comprises a tracking system that operates to verify that the patient is at said pre-set location at said pre-set time to participate in said therapeutic psychosocial activity and wherein said master control system cooperates with said tracking system to determine a time period that the patient was at said preset location and compares said time period with a scheduled time period for said therapeutic psychosocial activity to determine if the patent attended said therapeutic psychosocial activity for the entire said scheduled time period.

10. The system for encouraging therapeutic psychosocial activity of the patient of claim 9 wherein said therapeutic psychosocial activity is selected from the list consisting of taking a test, attending a therapy session, attending a self-help group meeting, or a medical appointment.

11. The system for encouraging therapeutic psychosocial activity of the patient of claim 1 further comprising compliant requirements that are transmitted to said portable communication device and one or more service providers, wherein said one or more service providers includes a financial provider that functions to receive financial information for depositing funds into an deposit account and for transferring a reward from said deposit account to a rewards account of the patient if the patient fulfills said compliant requirements.

12. A system for encouraging therapeutic psychosocial activity of a patient, the system comprising:
a master control system;
a portable communication device for use by the patient, said portable communication device is in communication with the master control system;
a testing device having testing software for obtaining test information and is coupled to said portable communication device which operates to communicate with said master control system and transmits said test information obtained by said testing device to said master control system;
a tracking system in communication with said master control system and operates to track a location of the patient and to verify that the patient is at a preset location at a preset time and further operates determine an amount of time the patient is at said preset location and compare the amount of time the patient is at said preset location with a time duration of a therapeutic psychosocial activity to determine if the patient complied with a compliant requirement; and
an identification system in communication with the master control system and operates to verify the identity of the patient using said testing device;
wherein said master control system includes analytics software that operates to compare test information obtained from a patient to previous test information obtained for the patient and then determines if there is any inconsistency and if said analytics software determines if there is any inconsistency, said analytics software creates a predictive outcome indicating said inconsistency with normal or expected results indicating the patient has a potential previously undiagnosed health problem and sends a notice of said inconsistency to an operator.

13. The system for encouraging therapeutic psychosocial activity of the patient of claim 12 further comprises a service provider in communication with said master control system wherein said service provider operates to transfer a reward to a patient when the patient has completed a compliant requirement.

14. The system for encouraging therapeutic psychosocial activity of the patient of claim 12 wherein said predictive outcome includes additional tests or tasks that should be assigned to the patient or other activities that should be performed by the patient.

15. The system for encouraging therapeutic psychosocial activity of the patient of claim 12 further comprising a transmittal schedule and wherein said transmittal schedule is created based on calculated predictive uncertainty or a calculated predictive risk for the patient.

16. The system for encouraging therapeutic psychosocial activity of the patient of claim 12 wherein said analytics software operates to use facial and body patterns and movements of the patient to determine the physical and emotional state of the patient and to calculate a predicted risk to make said predicted outcome.

17. The system for encouraging therapeutic psychosocial activity of the patient of claim 12 wherein said master control system operates such that if the patient performs a task or attends an activity that was not requested but is beneficial to the patient, said master control system operates to contact a service provider and request said service provider to transfer a reward to a patient.

18. The system for encouraging therapeutic psychosocial activity of the patient of claim 12 wherein said tracking system includes an imaging device that operates to obtain an image of the surroundings and is used by said master control system to identify a current location of the patient.

19. The system for encouraging therapeutic psychosocial activity of the patient of claim 12 wherein said identification system includes an imaging device that operates to obtain identifying information immediately before the patient takes a test, while taking said test and immediately after taking said test and if it determined that the patient was out of view of said imaging device during the taking of said test and if it is determined that the patient was out of view of said imaging device at any time during the taking of said test, said master control system operates to transmit a notice to said portable communication device of the patient that another test must be performed.

\* \* \* \* \*